United States Patent
Rogowski et al.

(10) Patent No.: US 11,234,954 B2
(45) Date of Patent: Feb. 1, 2022

(54) LOW-DOSE DOXEPIN FOR TREATMENT OF SLEEP DISORDERS IN ELDERLY PATIENTS

(71) Applicants: Pernix Sleep, Inc., Morristown, NJ (US); ProCom One, Inc., San Marcos, TX (US)

(72) Inventors: Roberta L. Rogowski, Rancho Santa Fe, CA (US); Susan Ellen Dube, Carlsbad, CA (US); Philip Jochelson, San Diego, CA (US); Neil Barton Kavey, Chappaqua, NY (US)

(73) Assignee: Currax Pharmaceuticals LLC, Brentwood, TN (US)

( * ) Notice: Subject to any disclaimer, the term of this patent is extended or adjusted under 35 U.S.C. 154(b) by 245 days.

(21) Appl. No.: 14/789,911

(22) Filed: Jul. 1, 2015

(65) Prior Publication Data

US 2016/0030383 A1    Feb. 4, 2016

Related U.S. Application Data

(63) Continuation of application No. 13/969,471, filed on Aug. 16, 2013, now abandoned, which is a continuation of application No. 13/621,665, filed on Sep. 17, 2012, now abandoned, which is a continuation of application No. 13/102,985, filed on May 6, 2011, now abandoned, which is a continuation of application No. 11/804,722, filed on May 18, 2007, now abandoned.

(60) Provisional application No. 60/801,823, filed on May 19, 2006.

(51) Int. Cl.
*A61K 31/355* (2006.01)
*A61K 31/335* (2006.01)

(52) U.S. Cl.
CPC ................. *A61K 31/335* (2013.01)

(58) Field of Classification Search
CPC .................................................... A61K 31/355
USPC ........................................................ 514/183
See application file for complete search history.

(56) References Cited

U.S. PATENT DOCUMENTS

| | | |
|---|---|---|
| 3,420,851 A | 1/1969 | Bloom et al. |
| 3,438,981 A | 4/1969 | Stach |
| 3,509,175 A | 4/1970 | Tretter |
| 4,110,438 A | 8/1978 | Gahwyler |
| 4,434,171 A | 2/1984 | Muller |
| 4,517,179 A | 5/1985 | Raghunathan |
| 4,833,154 A | 5/1989 | Jean-Louis et al. |
| 5,030,632 A | 7/1991 | Sterling |
| 5,116,852 A | 5/1992 | Gammans |
| 5,332,661 A | 7/1994 | Maciej Adamczyk et al. |
| 5,502,047 A | 3/1996 | Kavey |
| 5,585,115 A | 12/1996 | Sherwood et al. |
| 5,643,897 A | 7/1997 | Kavey |
| 5,725,883 A | 3/1998 | Staniforth et al. |
| 5,725,884 A | 3/1998 | Sherwood et al. |
| 5,733,578 A | 3/1998 | Hunter et al. |
| 5,741,524 A | 4/1998 | Staniforth et al. |
| 5,858,412 A | 1/1999 | Staniforth et al. |
| 5,866,166 A | 2/1999 | Staniforth et al. |
| 5,948,438 A | 9/1999 | Staniforth et al. |
| 5,965,166 A | 10/1999 | Hunter et al. |
| 6,103,219 A | 8/2000 | Sherwood et al. |
| 6,106,865 A | 8/2000 | Staniforth et al. |
| 6,211,229 B1 | 4/2001 | Kavey |
| 6,217,907 B1 | 4/2001 | Hunter et al. |
| 6,217,909 B1 | 4/2001 | Sherwood et al. |
| 6,219,674 B1 | 4/2001 | Classen |
| 6,344,487 B1 | 2/2002 | Kavey |
| 6,358,533 B2 | 3/2002 | Sherwood et al. |
| 6,391,337 B2 | 5/2002 | Hunter et al. |
| 6,395,303 B1 | 5/2002 | Straniforth et al. |
| 6,403,597 B1 | 6/2002 | Wilson et al. |
| 6,407,128 B1 | 6/2002 | Scaife et al. |
| 6,471,994 B1 | 10/2002 | Staniforth et al. |
| 6,521,261 B2 | 2/2003 | Sherwood et al. |
| 6,584,472 B2 | 6/2003 | Classen |
| 6,683,102 B2 | 1/2004 | Scaife et al. |
| 6,746,693 B2 | 6/2004 | Staniforth et al. |
| 6,852,336 B2 | 2/2005 | Hunter et al. |

(Continued)

FOREIGN PATENT DOCUMENTS

| | | |
|---|---|---|
| WO | WO-1999/40898 | 8/1999 |
| WO | WO-2000/010554 | 3/2000 |

(Continued)

OTHER PUBLICATIONS

Somaxon Somaxon Pharmaceutical Announces Positive Results in a Phase II Dose-Finding Study of Low-Dose Doxepin in Elderly Patients with Primary Sleep Maintainence Insomnia Somaxon Pharmaceuticals, Press Release, Apr. 21, 2005.*
Ancoli-Lsreal et al. 'Identification and treatment of sleep problems in the elderly' Sleep Medicine Reviews, 1(1), p. 3-17, 1997.*
Non-Final Office Action in U.S. Appl. No. 13/969,471, dated Feb. 27, 2014, 13 pages.
Non-Final Office Action in U.S. Appl. No. 13/621,665, dated Feb. 19, 2013, 16 pages.
Non-Final Office Action in U.S. Appl. No. 13/102,985, dated Mar. 16, 2012, 15 pages.

(Continued)

*Primary Examiner* — Yevgeny Valenrod
(74) *Attorney, Agent, or Firm* — Servilla Whitney LLC

(57) ABSTRACT

Methods of treating sleep disorders, particularly certain aspects of insomnia, in elderly patients (65 years and older) by administering initial daily dosages of doxepin of 1-3 mg. These ultra-low initial dosages are more effective in elderly versus non-elderly patients in decreasing wake time during sleep, latency to persistent sleep and wake time after sleep, and are particularly efficacious in treating those conditions in the last hour of an 8-hour sleep cycle. Also, the dosages described herein are safe for elderly individuals.

18 Claims, 2 Drawing Sheets

(56) References Cited

U.S. PATENT DOCUMENTS

| | | | |
|---|---|---|---|
| 6,858,231 | B2 | 2/2005 | Sherwood et al. |
| 6,866,867 | B2 | 3/2005 | Staniforth et al. |
| 6,936,277 | B2 | 8/2005 | Staniforth et al. |
| 7,135,196 | B2 | 11/2006 | Stockham |
| 7,179,488 | B2 | 2/2007 | Sherwood et al. |
| 7,276,536 | B2 | 10/2007 | Urata et al. |
| 7,542,872 | B2 | 6/2009 | Kadowaki et al. |
| 7,915,307 | B2 | 3/2011 | Baron et al. |
| 8,097,625 | B2 | 1/2012 | Lalji et al. |
| 2002/0037828 | A1 | 3/2002 | Wilson et al. |
| 2002/0197235 | A1 | 12/2002 | Moran |
| 2003/0175355 | A1 | 9/2003 | Tobyn et al. |
| 2003/0206978 | A1 | 11/2003 | Sherwood et al. |
| 2003/0235617 | A1 | 12/2003 | Martino et al. |
| 2004/0063721 | A1 | 4/2004 | Deecher et al. |
| 2004/0115142 | A1 | 6/2004 | Sherwood et al. |
| 2004/0224017 | A1 | 11/2004 | Mulye |
| 2004/0265374 | A1 | 12/2004 | Staniforth et al. |
| 2005/0013861 | A1 | 1/2005 | Sherwood et al. |
| 2005/0118261 | A1 | 6/2005 | Oien et al. |
| 2005/0123609 | A1 | 6/2005 | Hirish et al. |
| 2005/0147673 | A1 | 7/2005 | Staniforth et al. |
| 2005/0171160 | A1 | 8/2005 | Edgar et al. |
| 2005/0196439 | A1 | 9/2005 | Sherwood et al. |
| 2005/0214365 | A1 | 9/2005 | Yousef et al. |
| 2005/0239838 | A1 | 10/2005 | Edgar et al. |
| 2005/0256165 | A1 | 11/2005 | Staniforth et al. |
| 2006/0008522 | A1 | 1/2006 | Staniforth et al. |
| 2006/0228487 | A1 | 10/2006 | Schaible |
| 2007/0281990 | A1 | 12/2007 | Rogowski et al. |
| 2008/0058407 | A1 | 3/2008 | Baron et al. |
| 2008/0058408 | A1 | 3/2008 | Rogowski et al. |
| 2008/0182890 | A1 | 7/2008 | Jochelson et al. |
| 2009/0042971 | A1 | 2/2009 | Rogowski et al. |
| 2009/0042972 | A1 | 2/2009 | Rohowski et al. |
| 2009/0074862 | A1 | 3/2009 | Schioppi et al. |
| 2010/0105614 | A1 | 4/2010 | Jochelson et al. |
| 2010/0179214 | A1 | 7/2010 | Dube et al. |
| 2010/0179215 | A1 | 7/2010 | Dube et al. |
| 2010/0227916 | A1 | 9/2010 | Kavey et al. |
| 2011/0077200 | A1 | 3/2011 | Jochelson et al. |
| 2011/0166215 | A1 | 7/2011 | Casseday et al. |
| 2011/0178166 | A1 | 7/2011 | Rogowski et al. |
| 2011/0318412 | A1 | 12/2011 | Schioppi et al. |
| 2012/0088822 | A1 | 4/2012 | Rogowski et al. |
| 2012/0245222 | A1 | 9/2012 | Rogowski et al. |
| 2013/0096188 | A1 | 4/2013 | Dube et al. |
| 2013/0102658 | A1 | 4/2013 | Dube et al. |

FOREIGN PATENT DOCUMENTS

| | | |
|---|---|---|
| WO | WO-00/50025 | 8/2000 |
| WO | WO-2003/004009 | 1/2003 |
| WO | WO-2003/047519 | 6/2003 |
| WO | WO-2003/066029 | 8/2003 |
| WO | WO-2001/39749 | 6/2007 |
| WO | WO-2007/136845 | 11/2007 |
| WO | WO-2007/142810 | 12/2007 |
| WO | WO-2007/142811 | 12/2007 |

OTHER PUBLICATIONS

Non-Final Office Action in U.S. Appl. No. 11/804,722, dated Nov. 8, 2010, 12 pages.
Final Office Action in U.S. Appl. No. 13/969,471, dated Jan. 2, 2015, 15 pages.
Markku Partinen, Progress in Medicine, 2004, vol. 24, No. 7 222-232.
Merck Manual 17$^{th}$ ed. in Japanese, Nikkei BP, 1999, vol. 24 No. 7, p. 222-232.
The Japanese Journal of Psychiatry, 1999, vol. 4, No. 4, 333-340.
Pharmaceutical Regulatory Science, 1990, vol. 21, No. 1, 1-5.
Office Action in U.S. Appl. No. 13/492,559, dated Aug. 13, 2014.
JP Office Action in JP2013161145 dated Aug. 20, 2014.
Office Actions and Responses in U.S. Appl. No. 12/301,233.
European Search Report dated Aug. 14, 2009 for EP 07795135.8, filed May 18, 2007.
European Extended Search Report dated Mar. 2, 2011, for EP 07795135.8, filed May 18, 2007.
Electronic File History of U.S. Appl. No. 12/102,985, filed May 6, 2011 containing Office Action(s) dated Mar. 16, 2012 and Applicant(s) submissions Dec. 22, 2011 and Sep. 17, 2012 abandoned.
Electronic File History of U.S. Appl. No. 13/007,334, filed Jan. 14, 2011 (Abandoned) containing Office Action(s) dated Apr. 17, 2012, as of Sep. 25, 2012.
Electronic File History of U.S. Appl. No. 12/446,914, filed May 27, 2010 containing Office Action(s) dated Aug. 5, 2011, Jan. 20, 2012, Feb. 17, 2012 and Sep. 5, 2012 and Applicants Response(s) filed May 27, 2010, Jan. 20, 2012, and Aug. 17, 2012 as of Sep. 25, 2012.
Electronic File History of U.S. Appl. No. 12/101,917, filed Apr. 11, 2008 containing Office Action(s) dated Oct. 21, 2010, May 10, 2011, Jan. 12, 2012 and Nov. 21, 2012 Applicants Response(s) filed Dec. 2, 2008, Dec. 29, 2011 and Jul. 30, 2012 as of Dec. 17, 2012.
Electronic File History of U.S. Appl. No. 12/301,457, filed Apr. 12, 2010 containing Office Action9s) dated Jun. 7, 2012 and Applicants Response(s) filed Apr. 12, 2010 and Nov. 29, 2012 as of Dec. 17, 2012.
Electronic File History of U.S. Appl. No. 11/781,165, filed Jul. 20, 2007 (U.S. Pat. No. 7,915,307, issued Mar. 29, 2011) containing Office Action(s) dated Oct. 14, 2008, 0710712009, Sep. 29, 2009, Apr. 6, 2010, Oct. 21, 2010 and Nov. 12, 2010 and Applicant Response(s) filed Apr. 4, 2009, Dec. 4, 2009, Jul. 6, 2010 and Oct. 21, 2010 as of Jan. 11, 2011.
Electronic File History of U.S. Appl. No. 11/804,722, filed May 8, 2007(Abandoned) containing Office Actions dated Jun. 5, 2010, Nov. 8, 2010 and Jun. 2, 2011 and Applicant Respons(es) filed Oct. 15, 2010 as of Jan. 11, 2011 (now abandoned).
Electronic File History of U.S. Appl. No. 11/804,720, filed May 18, 2007 containing Office Action(s) dated Feb. 25, 2009, Nov. 30, 2009, Mar. 17, 2011, Jul. 27, 2011, and Aug. 16, 2011 and Applicant Response(s) filed Aug. 25, 2009, May 27, 2010, Dec. 27, 2010 and May 17, 2011 as of Dec. 16, 2011.
Electronic File History of U.S. Appl. No. 12/976,866, filed Dec. 27, 2010 containing Office Action(s) dated Oct. 19, 2011 and Dec. 8, 2011 and Applicants Response filed Sep. 30, 2011 as of Dec. 16, 2011.
Electronic File History of U.S. Appl. No. 12/022,628, filed Jan. 30, 2008 containing Office Action(s) dated Mar. 6, 2009 and Nov. 20, 2009, abandoned.
Electronic File History of U.S. Appl. No. 12/022,788, filed Jan. 30, 2008 containing Office Action(s) dated Mar. 9, 2009 and Dec. 9, 2009, abandoned.
Electronic File History of U.S. Appl. No. 11/867,595, filed Oct. 4, 2007 containing Office Action(s) dated Oct. 21, 2010, Apr. 20, 2011 and May 10, 2011 and Applicants Response(s) filed Apr. 20, 2011, Sep. 30, 2011 and Nov. 10, 2011 as of Dec. 16, 2011.
BPAI decision issued Dec. 11, 2012 in U.S. Appl. No. 11/804,720, filed May 18, 2007.
PCT International Search Report in PCT/US2007/011893, dated Aug. 11, 2007.
PCT International Preliminary Report on Patentability dated Dec. 4, 2008 in PCT/US2007/011893, filed May 18, 2007.
PCT International Search Report dated Mar. 18, 2008 in PCT/US2007/082569, filed Oct. 25, 2007.
PCT Partial International Search Report dated Apr. 8, 2008 in PCT/US2007/082569, filed Oct. 25, 2007.
PCT International Preliminary Report on Patentability dated May 7, 2009 in PCT/US2007/082569, filed Oct. 25, 2007.
PCT International Search Report dated Dec. 10, 2007 in PCT/US2007/016464, filed Jul. 20, 2007.
PCT International Preliminary Report on Patentability dated Jan. 20, 2009 in PCT/US2007/016464, filed Jul. 20, 2007.
PCT International Search Report dated Jan. 24, 2008 in PCT/US2007/012106, filed May 18, 2007.

(56) References Cited

OTHER PUBLICATIONS

PCT International Preliminary Report on Patentability & Written Opinion dated Nov. 21, 2008 in PCT/US2007/012106, filed May 18, 2007.
PCT International Search Report dated Jan. 24, 2008 in PCT/US2007/012105, filed May 18, 2007.
PCT International Search Report dated Jun. 17, 2008 in PCT/US2007/080492, filed Oct. 4, 2007.
PCT International Preliminary Report on Patentability and Written Opinion dated Apr. 7, 2009 in PCT/US2007/080492, filed Oct. 4, 2007.
PCT International Search Report and Written Opinion dated Jul. 29, 2008 in PCT/US2007/086682, filed Dec. 6, 2007.
PCT International Preliminary Report on Patentability and Written Opinion dated Jun. 18, 2009 in PCT/US2007/086682, filed Dec. 6, 2007.
PCT International Search Report and Written Opinion dated Aug. 13, 2009 in PCT/US2009/042912, filed May 5, 2009.
PCT International Search Report and Written Opinion dated Jan. 19, 2008 in PCT/US2008/060131, filed Apr. 11, 2008.
PCT International Preliminary Report on Patentability dated Oct. 13, 2009 in PCT/US2008/060131, filed Apr. 11, 2008.
PCT International Search Report and Written Opinion dated Jan. 21, 2008 in PCT/US2007/012107, filed May 18, 2007.
PCT International Preliminary Report on Patentability dated Nov. 21, 2008 in PCT/US2007/012107, filed May 18, 2007.
PCT Partial International Search Report dated Apr. 8, 2008, filed Oct. 25, 2007.
Council on Drugs, Evaluation of Doxepin Hydrochlroide (Sinequan), JAMA 215(12), Mar. 22, 1971, 1967-68.
Civil Docket of the U.S. District Court, District of Delaware, Case #1:11 cv-00537, RGA-MPT, printed Dec. 21, 2012 involving U.S. Pat. Nos. 6,211,229 and 7,915,307 of Somaxan Pharmaceuticals, Inc., pp. 1-5.
Abernethyl, et al., Absolute bioavailability of imipramine: Influence of food, *Psychopharmacology (Berl)*, 1984; 83(1):104-106.
ABPI (Association of the British Pharmaceutical Industry) Compendium of Data Sheets & SmPC's, 1999-2000; Pfizer Limited, p. 1158.
ABPI (Association of the British Pharmaceutical Industry) Compendium of Data Sheets and Summaries of Product Characteristics, 1996-1997; Pfizer Limited p. 751-752.
ABPI (Association of the British Pharmaceutical Industry) Data Sheet Compendium 1991-1992; Pfizer Limited, p. 1147-1149.
ABPI (Association of the British Pharmaceutical Industry) Data Sheet Compendium 1993-1994; Pfizer Limited, p. 1205-1207.
ABPI (Association of the British Pharmaceutical Industry) Data Sheet Compendium 1994-1995; Pfizer Limited, p. 1150-1151.
ABPI (Association of the British Pharmaceutical Industry) Data Sheet Compendium 1995-1996; Pfizer Limited, p. 1239-1240.
ABPI (Association of the British Pharmaceutical Industry) Medicines Compendium, 2002; Pfizer Limited, p. 1792-1793.
ABPI (Association of the British Pharmaceutical Industry) Data Sheet Compendium of Data Sheets and Summaries of Product Characteristics 1998-1999; Pfizer Limited, p. 970-971.
Adamzyk, et al., Quantitative determination of E- and Z-doxepin and E- and Z-desmethyldoxepin by high-performance liquid chromatography, *Ther Drug Monit.* 17(4):371-6 1995.
Adapin, Drug Side Effects, http://www.depression-guide.com/adapin.htm, 2005, 1-3.
Albemarle Pulmonary Medicine Associates, http://aomanc.com:80/PatientEducation/INSOMNIA.HTM, 2000, pp. 1-4.
Ambien (Zolpidem Tartrate) tablets CIV. Highlights of Prescribing Information. Revised Jun. 2009. Sanofi-Aventis U.S. LLC. p. 1-18.
Ambien (Zolpidem Tartrate) tablets CIV. Prescribing Information. Revised Jun. 2008. Sanofi-Aventis U.S. LLC. p. 1-22.
Ambien CR (zolipidem tartrate extended-release). Highlights of Prescribing Information. Package Insert. Jan. 2008, Sanofi-Aventis U.S. LLC. p. 1-7.

Ambien CR (zolpidem tartrate extended release) tablets—CIV. Full Prescribing Information. Sep. 2009. Web download: Jul. 6, 2010. http://products.sanofiaventis.us/ambien cr/ambiencr.html. p. 1-32.
Ambien CR (zolpidem tartrate extended release). Healthcare Professional Information. Healthcare Professionals. Help your insomnia patients meet the day on. Web download: Jul. 6, 2010. http://www.ambiencr.com/hcp/zolpidem-tartrate.aspx. p. 1-2.
Ancoli-Isreal, et al., Identification and Treatment of Sleep Problems in the Elderly, Review Article, *Sleep Medicine Reviews*, 1(1):3-17 1997.
Anon, Quitaxon 10 mg cp pellic sec. [Online] (2006), XP002507206, Retrieved from the Internet: URL:http://www.vidal.fr/MedicamenUquitaxon-14133.htm [retrieved on Dec. 8, 2008].
Approval data of the German drug regulatory authorities. DIMDI: AMIS—Public Part (AJ29).German Institute of Medical Documentation and Information within the scope of the Federal Ministry of Health. Pfizer Pharma GmBH. Sinquan 10 mg; capsules, SINQUAN 100; capsules; Sinquan 100 mg; capsules, SINQUAN 25 Intramuscular; solution; Sinquan 25 mg; capsules, Sinquan 50 mg; capsules, Sinquan 75 mg; capsules. Retrieved Nov. 16, 2005 from https://gripsdb.dimdi.de/session/051116152129299204 7/ 13docs.htm.
Badenhorst, et al., Determination of doxepin and desmethyldoxepin in human plasma using liquid chromatography-tandem mass spectrometry. *J Chromatogr B Biomed Sci Appl.*742:91-8 (2000).
Baldrick, Pharmaceutical Excipient Development: The Need for Preclinical Guidance. *Regul. Toxicol. Pharmacol.*, 32(2):210-8 2000.
Becker, Pharmacologic and Nonpharmacologic Treatments of Insomnia, *Neurol Clin.*, 23:1149-1163 2005.
Biggs, et al. Dosage schedule and plasma levels of doxepin and desmethyldoxepin. *J Clin Psychiatry.* 39(10):740-2 (1978).
Bogaert, et al. Plasma levels of the cis-and trans-isomers of doxepin and desmethyldoxepin after administration of doxepin to patients. *Arzneimittelforschung.* 31 (1):113-5 (1981).
Brunello, et al., Effect of Some Tricyclic and Nontricyclic Antidepressants on [H]Imiipramine Binding and Serotonin Uptake in Rat Cerebral Cortex After Prolonged Treatment. *Fundam Clin Pharmacol.*, 1: 327-333 (1987).
Brunswick, et al. Relationship between tricyclic antidepressant plasma levels and clinical response in patients treated with desipramine or doxepin. *Acta Psychiatr Scand.* 67(6):371-7 (1983).
Bundgaard, Ed. Design of Prodrugs: Bioreversible derivatives for various functional groups and chemical entities, Elsevier, Amsterdam (1985). Chapter 1. p. 1-92.
Burch, et al., Amitriptyline pharmacokinetics. A crossover study with single doses of amitriptyline and nortriptyline, *Psychopharmacolooy (Berl)*, 1981;74(1):35-42.
CBS.com, Ambien May Prompt Sleep-Eating; http://www.cbsnews.com/stories/2006/03/15/early show/health/ (2 pages).
Charman, Lipids, Lipophilic Drugs, and Oral Drug Delivery-Some Emerging Concepts. *J Pharm Sci.*, 89(8): 967-78 (2000).
Chen, Sleep, Depression and Antidepressants, *British Journal of Psychiatry*, 135: 385-402, (1979).
Chloral Hydrate Drug Information, Professional. Chloral Hydrate (Systemic). Drug Information Online. Drugs.com. Web. Jul. 6, 2010. http://www.drugs.com/mmx/chloralhydrate.html.
Claudino, et al., Antidepressants for Anorexia Nervosa (Review). *Cochrane Database Syst Rev.*, 1:1-39 (2006).
Conn, et al., Pattern of Use of Antidepressants in Long-Term Care Facilities for the Elderly, *Journal of Geriatric Psychiatry and Neurology*, vol. 5:4, p. 228-232.
Declerck et al., Increase in Slow-wave Sleep in Humans with the Serotonin-S2 *Antagonist Ritanserin. Curr Ther Res.*, 41 (4): 427-432 (1987).
Desyrel-trazadone hydrochloride tablet. Bristol Myers Squibb Company. Prescribing Information. Revised Feb. 2009.
Deuschle, et al. Doxepin and its metabolites in in depressed patients. *Psychopharmacology (Berl)* 131:19-22 (1997).
Digler, et al., High-performance liquid chromatographic determination of trans-doxepin and desmethyldoxepin *Arzneimittelforschung* 38(1): 1525-8 (1998).
Doxal. Laakeopas. Retrieved Nov. 28, 2005 from http://www.coronaria.fi/www/mtv3/laakkeet.php?id=299.

(56) References Cited

OTHER PUBLICATIONS

Doxal. Laakkeet. Retrieved Nov. 28, 2005 from http://ww.tohtori.fi/laakkeet/tuote. php3?10=412.
Doxepin. Find Treatment & Support. The most reliable information. Cancer.org. Web. Jul. 6, 2010. http://www.cancer.org/docroot/CDG/content/CDG doxepin.asp?internal=1.
Dugovic, et al., 5-HT2 Receptors could be Primarily Involved in the Regulation of Slow-wave Sleep in the Rat. *Euro J Pharma.*, 137:145-146 (1987).
Dunleavy, et al., Changes During Weeks in Effects of Tricyclic Drugs on the Human Sleeping Brain, *British Journal of Psychiatry*, 120: 663-672 (1972).
Ebert, et al. Treating insomnia: Current and investigaional pharmacological approaches. *Pharmacol Thera.*, 112(3): 612-629 (Mar. 2006).
Elavil-Amitriptyline Hydrochloride-amitriptyline hydrochloride tablet, film coated. Mutual Pharmaceutical Company, Inc. Revised Sep. 2007. p. 1-9.
Ereshefsky, et al. Pharmacokinetic factors affecting antidepressant drug clearance and clinical effect: evaluation of doxepir and imipramine—new data and review. *Clin. Chem.* 34(5):863-80 (1988).
Erman, et al., Comparative Efficacy of Zolpidem and Temazepam in Transient Insomnia, *Human Psychopharma Clin Exp.*, 16: 169-176 (2001).
Faulkner, et al. Comparative assays for doxepin and desmethyldoxepin using high-performance liquid chromatography and high-performance thin-layer chromatography. *J Pharm Sci.* 72(10):1165-7 (1983).
Faulkner, et al. Multiple-dose doxepin kinetics in depressed patients. *Clin Pharmacol Ther.* 34(4):509-15 (1983).
Fava, Weight Gain and Antidepressants. J *Clin Psychiatry*(61 Suppl) 11:37-41 (2000).
Fawcett, et al., Review of the results form clinical studies on the efficacy, safety and tolerability of mirtazapine for the treatment of patients with major depression, *J. Affective Disorders* (1998) 51: 267-285.
Friedel, et al. Relationship of blood levels of sinequan to clinical effects in the treatment of depression in aged patients. *In. Mendels J, editor. Amsterdam: Excerpta Medica.* p. 51-53 (1975).
Fulton, et al., Assessment of the Antidepressant Activity of Dothiepin and its Metabolites by Preclinical Tests. *J Affect Dis.*, 4: 261-269 (1982).
Georgotas, et al., Response of Depressive Symptoms to Nortriptyline, Phenelzine and Placebo *Br. J. Psychiatry* (1987) 151:102-106.
German Federal Gazette (BAnz) No. 240 of Dec. 22, 1992, p. 9545 (vol. 44).
Ghabrial, et al. Geometric isomerization of doxepin during its N-demethylation in humans. *Drug Metab Dispos.* 19(3):596-9 (1991).
Gillin, et al., Successful Separation of Depressed, Normal, and Insomniac Subjects by EEG Sleep Data, *Arch Gen Psychiatry*, vol. 36, pp. 85-90 (1979).
Green, Douglas O. Clinical importance of doxepin antidepressant plasma levels. *J Clin Psychiatry.* 39(5):481-2 (1978).
Grundstrom, et al., Sedative Properties of Doxepin in Comparison with Diazepam, *Psychopharmacology*, 54: 165-169 (1977).
Guidance for Industry SUPAC-IR/MR: Immediate Release and Modified Release Solid Oral Dosage Forms Manufacturing Equipment Addendum, Jan. 1999.
Hajak, et al., Nocturnal Melatonin Secretion and Sleep after Doxepin Administration in Chronic Primary Insomnia, *Pharmacopsychiatry* 29: 187-192, (1996).
Halcion-triazolam tablet. Pharmacia and Upjohn Company. Prescribing Information. Revised Jan. 2009.
Haritos, et al. Role of cytochrome P450 206 (CYP2D6) in the stereospecific metabolism of E-and Z''doxepin. *Pharmacogenentics.* 10(7):591-603 (2000).
Haritos, et al. Stereoselective measurement of E-and Z-doxepin and its N-desmethyl and hydroxylated metabolites by gas chromatography-mass spectrometry. *J Chromatoor B Biomed Sci Appl.* 736(1-2):201-8 (1999).

Hartmann, et al., The Effects of Long Term Administration of Psychotropic Drugs on Human Sleep: III. The Effects of Amitriptyline, *Psychopharmacologia*, 33: 185-202(1973).
Hartmann, Peter M., Miratzapine: A Newer Antidepressant *American Family Physician* (1999) 1-5.
Hartter, et al. The N-demethylation of the doxepin isomers is mainly catalyzed by the polymorphic CYP2C19. *Pharm Res.* 19(7): 1034-7 (2002).
Haute Autorite De Sante (France): Avis Dec. 13, 2006 [Online] 2006, XP002507207; Retrieved from the Internet: URL:http://www.hassante.fr/portail/jcms/c475580/quitaxon> [retrieved on Dec. 8, 2008].
Heal, et al., Comparative Pharmacology of Dothiepin, its Metabolites, and other Antidepressant Drugs. *Drug Dev Res.*, 27: 121-135 (1992).
Hellberg, et al., The Hydrolysis of the Prostaglandin Analog Prodrug Bimatoprost to 17-Phenyl-Trinor PGF2 by Human and Rabbit Ocular Tissue. *J Ocul Pharmacol Ther.*, 19(2): 97-103 (2003).
Higuchi, et al., Pro-Drugs as Novel Delivery Systems, A.C.S. Symposium Series, *American Chemical Society*; vol. 14, (19 75) Title Pages Only.
Hobbs, Distribution and Metabolism of Doxepin, *Biochem. Pharmacol.*, 18(8): 1941-1954 (1969).
Hohagen, et al., Treatment of Primary Insomnia with Trimipramine: An Alternative to Benzodiazepine Hypnotics? *Eur Arch Psychiatry Clin Neurosci.*, 244(2): 65-72 (1994).
Hrdina, et al. Antidepressant plasma levels and clinical response in depressed patients treated with oxaprotiline and doxepin. *Int Clin Psychopharmacol.* Jul 3(3):205-14 (1988).
Hrdina, et al. Cis-and trans-isomers of doxepin and desmethyldoxepin in the plasma of depressed patients treated with doxepin. *Ther Drug Monit.* 12(2):129-33 (1990).
Hsu, et al., Low-Dose Doxepin in the treatment of primary insomnia, *Sleep*, 28: suppl, p. A50 (2005).
Jacobsen, Low-Dose Trazodone as a Hypnotic in Patients Treated with MAOIs and Other Psychotropics: A Pilot Study, *Journal of Clinical Psychiatry*, 51: 298-392 (1990).
Joyce, et al. Doxepin plasma concentrations in clinical practice. Could there be a pharmacokinetic explanation for low concentrations *Clin Pharmacokinet.* 10(4):365-70 (1985).
Kales, et al., Effects of Sinequan on sleep of Insomniac Subjects, *Sleep Study Abstracts*, p. 93, (1972).
Kirchheimer, et al. Contributions of CYP2D6, CYP2C9 and CYP2C19 to the biotransformation of E-and Z-doxepin in healthy volunteers. *Pharmacogenetics.* 12(7):571-80 (2002).
Kline, et al. Doxepin and Desmethyldoxepin Serum Levels and Clinical Response. In: Gottschalk LA MM, editor. Pharmacokinetics of psychoactive drugs: blood levels and clinical response. *New York: Spectrum Press*, p. 221-28 (1976).
Krakowski, Seminar on Psychopharmacology—Auspices of Academy of Psychosomatic Medicine, Dec. 8-9, 1968 Freeport, Grand Bahama Island, Psychosomatics, pp. 7-63 (1968).
Laimer, et al., Effect of Mirtazapine Treatment on Body Composition and Metabolism, J Clin. Psychiatry, 67(3): 421-524 (2006).
Lapp, Chronic Fatigue Syndrome is a Real Disease, North Carolina Family Physician, 43:1 (1992).
Leucht, et al. Doxepin plasma concentrations: is there really a therapeutic range *J Clin Psychopharmacol.* 21 (4):432-9 (2001).
Linnoila, et al. Clomipramine and doxepin in depressive neurosis. Plasma levels and therapeutic response. *Arch Gen Psychiatry.* 37(11):1295-9. (1980).
Luchtefeld, Answers to the Most Common Questions Regarding Prescription Drugs—Safeguard Your Health, Jenry Consulting 1999, http://www.grandtimes.com/Answer Drugs.html, 1-3.
Lunesta (Eszopiclone) Tablets 1 mg, 2 mg, 3 mg. Prescribing Information. Sepracor Inc. (Jan. 2009) p. 1-2.
Luo, et al., The Quaternary Ammonium Linked Glucuronide of Doxepin: A Major Metabolite in Depressed Patients treated with Doxepin. *Drug Metab Dispos.*, 19(3): 722-724 (1991).
Manning, et al., Central Nervous System Effects of Meclizine and Dimenhydrinate: Evidence of Acute Tolerance to Antihistamines. *J. Clin. Psychiatry*, 32:996-1002 (1992).

(56) References Cited

OTHER PUBLICATIONS

Masaki, et al., Involvement of Hypothalamic Histamine H1 Receptor in the Regulation of Feeding Rhythm and Obesity, Diabetes, 53(9): 2250-2260 (2004).
Masaki, et al., The Hypothalamic H1 Receptor: A Novel Therapeutic Target for Disrupting Diurnal Feeding Rhythm and Obesity. *Trends Pharmacol Sci.*, 27(5): 279-284 (2006).
Mayers, et al., Antidepressants and their effect on sleep, *Hum Psychopharmacol.*, 20(8):533-559 (Dec. 2005).
Mealy, et al., Drugs Under Development for the Treatment of Psychiatric Disorders. *Drugs Fut.* 31 (3): 266-284 (2006).
Mercer, et al., Dietary Induced Anorexia: A Review of Involvement of the Histominergic System, *J Am Coll Nutr.*, 15(3): 223-230 (1996).
Midha, et al. Stereoselective pharmacokinetics of doxepin isomers. *Eur J Clin Pharmacol.* 42(5):539-44 (1992).
Moody, et al., Biotransformation of Doxepin by Cunninghamella Elegans, *Drug Metab Dispo.*, 27(10): 1157-1164 (1999).
Narasimhachari, et al., N-Alkylation of Secondary Amine Tricyclic Antidepressants as a General Method for Their Quantitation by GC-MS-SIM Technique. *Analytical Lett.* 12(81):77-88 (1979).
National Academy of Sciences, Sleeping Pills, Insomnia, and Medical Practice, *Institute of Medicine*, 32-33, 103, 125, 149, 169, 198, (1979).
Natrol Melatonin 3 mg. 60 Tablets. Dietary Supplement. Manufactured by NATROL, Inc. Label.
Neubauer D., Sleep Problems in the Elderly. Am Fam Physician. 59(9): 2551-2558 (May 1999).
Newcomer, et al., The Metabolic Effects of Antipsychotic Medications, *Can J Psychiatry*, 51 (8): 480-491 (2006).
Nicholson, et al., Modulation of sleep by trimipramine in man, *European Journal of Clinical Pharmacol*, 37: 145-150 (1989).
Nierenberg, et al., Management of Monoamine Oxidase Inhibitor-Associated Insomnia with Trazodone, *Journal of Clinical Psychopharmacol*, vol. 9 No. 1, p. 42-45 (1989).
NyQuil Oral. Drugs & Medications. WebMD. Web download: Jul. 6, 2010. http://www.webmd.com/drugs/drug-6104-NyQuil+Oral.aspx?drugid=6104&druoname=NyQuil+Oral&source=1. p. 1-3.
NyQuil Cold & Flu. Nightime Relief. Acetaminophen, Doxylamine, Dextromethorphan, Alcohyl 10%. 6 Fl Oz. Vicks Label. 2 pages.
Nytol Quickcaps with Diphenhydramine HCI. Nightime Sleep-Aid. 72 Caplets. Label. 4 pages.
Nytol Oral. Drugs & Medications—WebMD. Web download: Jul. 6, 2010. http://www.webmd.com/drugs/drug-10538Nytol+Oral.aspx?drugid=10538&drugname=Nytol+Oral&source=O. p. 1-2.
O'Brien, et al. GLC determination of doxepin plasma levels. *J Pharm Sci.* 65(7): 1068-9 (1976).
Ookuma, et al., Evidence for Feeding Elicited Through Antihistaminergic Effects of Tricyclic Antidepressants in the Rat Hypothalamus. *Psychopharmacology (Berln)*.101(4): 481-485 (1990).
Orthen-Gambill, et al., Differential Effects of Psychotropic Drugs on Feeding in Rats: Is Histamine Blockade Involved? *Pharmacol Biochem Behav.*, 36(4): 837-841 (1990).
Orthen-Gambill, Antihistaminic Drugs Increase Feeding, While Histidine Suppresses Feeding in Rats, *Pharmacol Biochem Behav.*, 31(1): 81-86 (1988).
Palvimaki, et al. Interactions of selective serotonin reuptake inhibitors with the serotonin 5-HT2C陆ceptor. *Phychopharmacology*, 126(3): 234-240 (1996).
Patient Information Leaflet, Sinequan™ (doxepin), United Kingdom, p. 1-2 (2002).
Pecknold, et al., Trimipramine, Anxiety, Depression and Sleep, *Drugs*, vol. 38: Suppl. 1, p. 25-31 (1989).
Pfizer, Chemist Review of NOA 17-516, Division of Neurophamacological Drug Products, Chemists Review #3, (1973).
Pfizer, New Drug Application NOA 16-798, Sinequan in Capsules; Research, Review & Findings Report; pp. 1-174 Approved in 1978 [Relevant pp. 46-47, 54, 57, 59.
Pharmaca Fennica. Published by the Finnish Centre for Medicine Information (Laaketietokeskus); SR Doxal; (1992).
Pharmaca Fennica. Published by the Finnish Centre for Medicine Information (Laaketietokeskus); SR Doxal; 612-613 (1988).
Pharmaca Fennica. Published by the Finnish Centre for Medicine Information (Laaketietokeskus); SR Doxal; 714 (1991).
Pharmaca Fennica. Published by the Finnish Centre for Medicine Information (Laaketietokeskus); SR Doxal; 738 (1993).
Pharmaca Fennica. Published by the Finnish Centre for Medicine Information (Laaketietokeskus); SR Doxal; 830 (1995).
Pharmaca Fennica. Published by the Finnish Centre for Medicine Information (Laaketietokeskus); Ye R Doxal; 534-535 (2000).
Pharmaca Fennica. Published by the Finnish Centre for Medicine Information (Laakevalmisteet); SR Sinequan; 845-846 (1993).
Pharmassure. Standardized. Valerian. Herbal Supplement. Minimumum 0.8% Valerenic Acids (2mg). 250 mg. 60 So 仕 gelCapsules. Distributed by PharmAssure, Inc. Label.
Phillips, et al., Sleep Disorders in the Elderly, *Sleep Medicine* 2:99-114 (2001).
Physician's Desk Reference, 1999 ed., Medical Economics Company, Montvale NJ pp. 539-541 (trazadone).
Physician's Desk Reference, 2000 ed., Medical Economics Company, Montvale NJ pp. 2366-2367 (Doxepine HC).
Physician's Desk Reference, 2000 ed., Medical Economics Company, Montvale NJ pp. 3323-3324 (trimipramine maleate).
Physician's Desk Reference, 2000 ed., Medical Economics Company, Montvale NJ pp. 549-551 (Amitriptyline HC).
Physician's Desk Reference, Litton Industries, p. 1211, 93, (1976).
Physician's Desk Reference, p. 1310-1312, (1990).
Physician's Desk Reference, p. 1849-1850, (1990).
Physician's Desk Reference, p. 2434-2435, (1990).
Pinder, et al. Doxepin up-to date: a review of its pharmacological properties and therapeutic efficacy with particular reference to depression. *Drugs*. 13(3):161-218 (1977).
Polish Drug Application for SINEQUAN 10 mg capsules. 01474/93. p. 1-4 with attached Annex in 4 pages.
Polish Drug Application for SINEQUAN 25 mg capsules. 01475/93. p. 1-4 with attached Annex in 4 pages.
Pollack, Is Biotechnology Losing Its Nerve? NY Times (Feb. 29, 2004).
Pollack et al., The Selective GABA Reuptake Inhibitor Tiagabine for the Treatment of Generalized Anxiety Disorder: Results of a Placebo-Controlled Study, J Clin Psychiatry 66: 401-1408(Nov. 2005).
Powell, et al. Compendium of Excipients for Parenteral Formulations, *PDA J Pharm Sci Technol.* 52(2): 238-311 (1998).
Prakash, et al. Deuterium Labeling of the Antidepressant Drug Doxepin for Disposition Studies in Human Subjects. *J Lab Comp Radiopharma.* 28(9): 1037-47(1990).
Remington: The Science and Practice of Pharmacy, 21st Ed., Lippincott Williams & Wilkins (2006). Table of Contents Only.
Restoril—Temazepam capsule. Mallinckrodt Inc. Prescribing Information. Revised Mar. 2006. p. 1-8.
Ribbentrop, et al., Pharmacologic studies of doxepin, an antidepressive agent with centrally anticholinergic and sedative effects. Arzneimittelforschung. 15:863-68 (1965).Translation of Abstract only.
Richardson, et al., Tolerance to Daytime Sedative Effects of H1 Antihistamines. *J Clin Psychopharmacol.* 22(5): 511-515 (2002).
Richelson et al., Antagonism by Antidepressants of Neurotransmitter Receptors of Normal Human Brain in Vitro, *J Pharmacol Exp Ther.* 230(1): 94-102(1984).
Richelson, Tricyclic Antidepressants and Histamine H1 Receptors, *Mayo Clin Proc.*, 54:669-674, (1979).
Roche, Bioreversible Carriers in Drug Design: Theory and Application, *Pergamon Press: New York*, (1987) Contents pages only.
Rodenbeck et al., The sleep-improving effects of doxepin are paralleled by a normalized plasma co同 1 solsecretion in primary insomnia, Psychopharma. 170(4): 423-428 (2003).
Rosseel, et al. Quantitative GLC determination of cis-and trans-isomers of doxepin and desmethyldoxepin. *J Pharm Sci.* 67(6):802-5 (1978).
Roth, et al., Psychopharmacolodgy: The Effectsof Doxepin HCI on Sleep and Depression, *Journal of Clinical Psychiatry*, 43:9, p. 366-368 (1982).

(56) References Cited

OTHER PUBLICATIONS

Roth, et al., Efficacy and Safety of Doxepin 1,3, and 6mg in Elderly Adults with Primary Insomnia, Sleep, 29: Abstract Suppl. #0706, A239-A240 (2006).
Roth, et al., Efficacy and Safety of Zolpidem-MR: A Double-Blind, Placebo-Controlled Study in Adults with Primary Insomnia, *Sleep Med.* 7(5): 397-406 (2006).
Roth, et al., Efficacy and Safety of Doxepin 1 mg, 3mg, and 6mg in Adults with Primary Insomnia, *Sleep*, 30(11): 1555-1561 (Nov. 2007).
ROZEREM (ramelteon) tablets. Highlights of Prescribing Information. Takeda Pharmaceuticals. Revised Oct. 2008. p. 1-6.
Saul, Stephanie, Study Links Ambien Use to Unconscious Food Forays, The New York Times http://www.nytimes.com/2006/03/14/health/14sleep.html (4 pages).
Scharf et al., Efficacy and Safety of Doxepin 1 mg, 3 mg, and 6 mg in Elderly Patients With Primary Insomnia: A Randomized, Double'Blind, Placebo-Controlled Crossover Study. *J Clin Psychiatry* 69(10): 1557-1564 (Oct. 2008).
Schatzberg, et al., "Hypnotics" Manual of Clinical Psychopharmacology, *American Psychiatric Press, Inc.*, Washington D.C., 173-189 (1986).
Schweitzer, et al., Sleepiness and Performance During Three-Day Administration of Cetirizine or Diphenhydramine. *J Allergy Clin Immunol.* 94(4): 716-724(1994).
Seifritz E. Contribution of Sleep Physiology to Depressive Pathophysiology, *Neuropsychopharmacology* 25(5) S1: S85-S88 (Nov. 2001).
Shu, et al., Identification of Phenolic Doxepin Glucuronides from Patient Urine and Rat Bile. *Drug Metab Disp.* 18(6): 1096-1099 (1990).
Shu, et al., The Identification of Urinary Metabolites of Doxepin in Patients. Drug Metabolism & Disposition, *Drug Metabolism & Disposition*, 18(5): 735-741 (1990).
Silenor (doxepin) Drug Description. RXList: Apr. 2, 2010. p. 1.
Silenor (doxepin) Prescribing Information. Revised Mar. 2010.
Sinequan (doxepin HCI) Capsules Oral Concentrate. Prescribing Information. Revised Oct. 2008. p. 1-13.
Sinequan (Doxepin, Adapin): A guide to sinequan side effects, depression guide.com (2005). Web download: Jul. 6, 2010. http://www.depression-guide.com/sinequan.htm. p. 1-3.
Sinequan Dosage. eMEDTV. Clinaero, Inc. Updated/reviewed Apr. 2, 2007. Web download: Jul. 6, 2010. http://depression.emedtv.com/sinequan/sinequan-dosage.html. p. 1-2.
Sokoliess, et al."Separation of (Z)-and (E)—isomers of thioxanthene and dibenz[b,e]oxepin derivatives with calixarenes and resorcinarenes as additives in nonaqueous capillary electrophoresis."Electrophoresis. 24(10):1648-57 (2003).
Somaxon Pharmaceuticals Announces the Completion of Enrollment in a Phase I Study Evaluating S0-101 for the Treatment of Sleep Maintenance Insomnia in Adults, Somaxon Pharmaceuticals, p. 1 (Oct. 7, 2004).
Somaxon Pharmaceuticals Announces Positive Results in aP hase I Dose-Finding Study of Low-Dose Doxepin in Adults with Primary Sleep Maintenance Insomnia, Somaxon Pharmaceuticals, p. 1-2 (Jan. 6, 2005).
Somaxon Pharmaceuticals Announces Positive Results in aP hase I Dose-Finding Study of Low-Dose Doxepin in Elderly Patients with Primary Sleep Maintenance Insomnia, Somaxon Pharmaceuticals, p. 1-3 (Apr. 21, 2005).
Somaxon Pharmaceuticals, Inc. Initiates Phase III Clinical Trials of SILENOR™ in Patients with Insomnia, Somaxon Pharmaceuticals Press Release, San Diego, CA, p. 1-3 (Jun. 9, 2005).
Somaxon Pharmaceuticals, Inc. Initiates Second Phase III Clinical Trials of SILENOR™, Somaxon Pharmaceuticals Press Release, San Diego, CA (Sep. 20, 2005).
Somaxon Pharmaceuticals Announces Positive Phase 3 Results with SILENORR for the Treatment of Adults with Chronic Insomnia, Somaxon Pharmaceuticals, p. 1-5 (Apr. 10, 2006).
Somaxon Pharmaceuticals Announces Presentation of Phase I SILENORR Data at the Associated Professional Sleep Societies Annual Meeting, Somaxon Pharmaceuticals, p. 1-2 (Jun. 20, 2006).
Somaxon Pharmaceuticals Provides Update on SILENORR Development Program for the Treatment of Insomnia, Somaxon Pharmaceuticals, p. 1-5 (Jul. 19, 2006).
Somaxon Pharmaceuticals Provides Update on Preclinical and Clinical Programs for SILENOR™, Somaxon Pharmaceuticals Press Release, San Diego, CA, p. 1-3 (Sep. 11, 2006).
Somaxon Pharmaceuticals' SILENORR Demonstrates Positive Results in a Phase 3 Transient Insomnia Clinical Trial, Somaxon Pharmaceuticals, p. 1-5, (Oct. 23, 2006).
Somaxon Pharmaceuticals' SILENORR Demonstrates Positive Results in its Third Phase 3 Clinical Trial in Insomnia, Somaxon Pharmaceuticals, p. 1-6, (Nov. 20, 2006).
Somaxon Pharmaceuticals' SILENORR Demonstrates Positive Results in Long-Term Phase 3 Clinical Trial in Elderly Patients with Insomnia, Somaxon Pharmaceuticals, p. 1-7 (Dec. 18, 2006).
Somaxon Pharmaceuticals Provides Update on SILENOR™ Preclinical Program, Somaxon Pharmaceuticals Press Release, San Diego, CA, p. 1-7 (Feb. 13, 2007).
Somaxon Pharmaceuticals Provides Update on SILENOR™ Development Program, Somaxon Pharmaceuticals Press Release, San Diego, CA, p. 1-3 (May 9, 2007).
Somaxon Pharmaceuticals Announces Completion of 26-Week Transgenic Mouse Carcinogenicity Study of SILENOR™, Somaxon Pharmaceuticals Press Release, San Diego, CA, p. 1-3 (Jan. 9, 2008).
Somaxon Pharmaceuticals Submits New Drug Application for SILENOR™ for the Treatment of Insomnia, Somaxon Pharmaceuticals Press Release, San Diego, CA, p. 1 -6 (Jan. 31, 2008).
Somaxon Pharmaceuticals Announces Acceptance for Filing of New Drug Application for SILENOR™ for the Treatment of Insomnia, Somaxon Pharmaceuticals Press Release, San Diego, CA, p. 1-5 (Apr. 15, 2008).
Somaxon Pharmaceuticals Announces Data to be Presented at American Psychiatric Association 161st Annual Meeting, Somaxon Pharmaceuticals Press Release, San Diego, CA (May 2, 2008).
Somaxon Pharmaceuticals Announces Data to be Presented at American Psychiatric Association 161st Annual Meeting, Somaxon Pharmaceuticals Press Release, San Diego, CA, p. 1-7 (May 7, 2008).
Somaxon Pharmaceuticals to Present Data at the 22nd Annual Meeting of the Associated Professional Sleep Societies, Somaxon Pharmaceuticals Press Release, San Diego, CA (Jun. 4, 2008).
Somaxon Pharmaceuticals' SILENORR Data Presented at the 22nd Annual Meeting of the Associated Professional Sleep Societies, Somaxon Pharmaceuticals Press Release, San Diego, CA, p. 1-4 (Jun. 12, 2008).
Somaxon Pharmaceuticals Presents Pharmacological Data on Doxepin at the 21st European College of Neuropsychopharmacology Congress, Somaxon Pharmaceuticals Press Release, San Diego, CA, p. 1-3 (Sep. 2, 2008).
Somaxon Pharmaceuticals Receives Complete Response Letter from the FDA for SILENORR (Doxepin), Somaxon Pharmaceuticals Press Release, San Diego, CA, p. 1-3 (Feb. 26, 2009).
Somaxon Pharmaceuticals Provides Update on New Drug Application for SILENORR (Doxepin) for the Treatment of Insomnia, Somaxon Pharmaceuticals Press Release, San Diego, CA, p. 1-4 (Apr. 7, 2009).
Somaxon Pharmaceuticals Presents Analyses of Silenor Clinical Data at the American Psychiatric Association Annual Meeting, Somaxon Pharmaceuticals Press Release, San Diego, CA, p. 1-6 (May 20, 2009).
Somaxon Pharmaceuticals Resubmits New Drug Application for SILENORR (Doxepin) for the Treatment of Insomnia, Somaxon Pharmaceuticals Press Release, San Diego, CA, p. 1-4 (Jun. 4, 2009).
Somaxon Pharmaceuticals Receives Complete Response Letter from the FDA for SILENORR NDA, Somaxon Pharmaceuticals Press Release, San Diego, CA, p. 1-3 (Dec. 7, 2009).

(56) References Cited

OTHER PUBLICATIONS

Somaxon Pharmaceuticals Scheduled to Meet with FDA to Discuss Complete Response Letter for SILENORR NDA, Somaxon Pharmaceuticals Press Release, San Diego, CA (Dec. 17, 2009).
Somaxon Pharmaceuticals Provides Update on New Drug Application for SILENORR for the Treatment of Insomnia, Somaxon Pharmaceuticals Press Release, San Diego, CA, p. 1-3 (Jan. 21, 2010).
Somaxon Pharmaceuticals Announces FDA Approval of SILENORR (Doxepin) for the Treatment of Insomnia, Somaxon Pharmaceuticals Press Release, San Diego, CA, p. 1-5 (Mar. 18, 2010).
Sominex Caplets. Nightime sleep-aid—Diphenhydramine. GlaxoSmithKline. Consumer Healthcare, L.P. Label. 3 pages.
Sominex Oral. Drugs & Medications. WebMD. Web download: Jul. 6, 2010. http://www.webmd.com/drugs/drug-15470-Sominex+Oral.asox?druoid=1547Q&drugname=Sominex+Oral&source=1. p. 1-3.
Sonata (Zaleplon) Capsules. Prescribing Information. King Pharmaceuticals. Feb. 2009. p. 1-15.
Sonata Official FDA information, side effects and uses. Drug Information Online. Drugs.com. Web. Jul. 6, 2010. http://www.drugs.com/pro/sonata.html. p. 1-22.
Stella et al. Prodrugs: Challenges and Rewards, Part 1, Biotechnology: Pharmaceutical Aspects, p. 24, 2007.
Stimmel, et al., Mirtazapine: An Antidepressant with Noradrenergic and Specific Serotonergic Effects, *Pharmacotherapy* (1997) 17(1): 10-21.
Summary Basis for approval of ADAPIN (1972) Pursuant to FOIA Request filed in 1981.
Summary Basis for Approval of SINEQUAN (1973); Pursuant to FOIA Request filed in 1996 (sedative, tranquilizer and sleep effects mentioned for example on pp. 50, 54-56, 58-59).
Technical Information/Summary of Drug Characteristics (SPC), Pfizer, p. 1-4, (2004).
Thase, Michael E., Antidepressant Treatment of the Depressed Patient with Insomnia *J. Clin. Psychiatry* (1999) 60 (Suppl. 17): 28-31.
Tylenol PM. Extra Strength Pain Reliever. Nighttime Sleep Aid. Contains Acetaminophen, Diphenhydramine HCI. 50 Caplets. Label. 4 pages.
Tylenol PM Extra Strength Pain Reliever. Nighttime Sleep Aid. Contains Acetaminophen, Diphenhydramine HCI. 24 Geltabs. Label. 4 pages.
Tylenol PM Oral. Drugs & Medications—WebMD. Web download: Jul. 6, 2010. http://www.webmd.com/drugs/drug74986Tylenol+PM+Oralaspx?drugid=74986&druQname=Tylenol+PM+Oral&source=1. p. 1-3.
Vincent, et al., Use of Human Sleep as a Test of Drug's Psychotropic Action with Doxepin as an example, *Bordeaux Medical*, No. 10, 2650-51, 2653-54, 2657-57,and 2661 (1971).
Virtanen, et al. Radioimmunoassay for doxepin and desmethyldoxepin. *Acta Pharmacol Toxicol* (Copenh). 47(4):274-8 (1980).
Voshaar, et al., Zolpidem is not Superior to Temazepam with Respect to Rebound Insomnia: A Controlled Study. *Eur Neuropsychopharrhacol.* 14(4): 301-306 (2004).
Ward, et al. Doxepin plasma levels and therapeutic response in depression: preliminary findings. *J Clin Psvchopharmacol.* 2(2):126-8 (1982).
Ware, Tricyclic Antidepressants in the Treatment of Insomnia, *Journal of Clinical Psychiatry*, 44 [9, Section 2]: 25-28 (1983).
Wheatley, Prescribing Short-Acting Hypnosedatives: Current Recommendations from a Safety Perspective, *Drug Safety* 7(2): 106-115 (1992).
Wolfe, Antidepressant Withdrawal Reactions. Am Fam Physician. 56(2): 455-462, (1997).
Wyatt, et al., Carbon 13 NMR OF Z-and E-Doxepin Hydrochloride. Applied Spectroscopy. 49(4):538-542 (1986).
Yan, et al. Stereoselective in vivo and in vitro studies on the metabolism of doxepin and N-desmethyldoxepin. *Xenobiotica.* 27(12): 1245-1257 (1997).
Yan, J., et al., Stereoselective and simultaneous measurement of cis-and trans-isomers of doxepin and N-desmethyldoxepin in plasma or urine by high-performance liquid chromatography, *Journal of Chromatography B: Biomedical Sciences & Applications.* vol. 691, No. 1, Mar. 28, 1997, 131-138.
Zaleplon Capsules. Drug Information Online. Drugs.com. Web download: Aug. 25, 2009. http://www.drugs.com/pro/zaleplon.html?printable=1. and Package Label. *Augobindo Pharma Ltd*. p. 1-23.
Ziegler, et al. Doxepin kinetics. *Clin Pharmacol Ther.* 23(5):573-9 (1978).
Zimmermann, et al., Epidemiology, implications and mechanisms underlying drug induced weight gain in psychiatric patients *J. Psychiatric Research* (2003) 37: 193-220.
Zung, Effect of Antidepressant Drugs on Sleeping and Dreaming, Excerpta Medica Foundation International Congress Series, No. 150, 1824-1826 (1968).

\* cited by examiner

PSG Parameters

DOXEPIN PLASMA PROFILE CONCENTRATIONS (ng/mL)

LOW-DOSE DOXEPIN FOR TREATMENT OF SLEEP DISORDERS IN ELDERLY PATIENTS

RELATED APPLICATION

This application is a continuation of U.S. patent application Ser. No. 13/102,985, filed May 6, 2011, which is a continuation of U.S. patent application Ser. No. 11/804,722, filed May 18, 2007, which claims priority under 35 U.S.C. 119 to U.S. Provisional Application No. 60/801,823, filed May 19, 2006, the entire contents of which are incorporated herein by reference.

FIELD OF THE INVENTION

The present invention relates to the use of ultra-low doses of doxepin (1-3 milligrams) for treatment of sleep disorders, particularly insomnia, in individuals 65 years or older.

BACKGROUND OF THE INVENTION

Sleep is essential for health and quality of life. Insomnia is a growing health problem in the United States. It is believed that more than 10-15 million people suffer from chronic insomnia and up to an additional 70 million people suffer from some form of insomnia each year. Insomnia is a condition characterized by difficulty falling asleep (sleep onset), waking frequently during the night (fragmented sleep), waking too early (premature final awakening), and/or waking up feeling un-refreshed. In the National Sleep Foundation's (NSF) Sleep in America Poll 2005, 42% of survey respondents reported that they awoke frequently during the night, 22% of adults reported waking too early and not being able to return to sleep and 38% reported waking and feeling un-refreshed.

Sleep maintenance difficulty is a significant problem for many primary care patients with chronic insomnia, including depressed patients, medically ill populations, especially those with pain symptoms, and the elderly.

In elderly populations (i.e., patients over the age of 65 years), there are several sleep disorders that are often difficult to satisfactorily address or manage with available medications. Many elderly patients suffer from premature final awakening or terminal insomnia, in which they awaken for the day prior to the end of a normal 8-hour sleep period. Although some conventional medications can extend sleep time, they often fail to satisfactorily address the issue. In some instances, sleep is not extended into the final (eighth) hour of the sleep period, so that the patient still prematurely terminate sleep prior to the end of the sleep period, particularly during the last hour of an 8-hour period. If the dosage of medication is sufficient to extend sleep into or through the eighth hour of the sleep period, the patients often suffer from post-sleep amnesia or memory loss, or experience sedation after awakening that can interfere with normal activities, including driving, operation of other equipment, concentration, and normal mental function.

Other elderly patients suffer from fragmented sleep in the final hour of sleep, exhibiting disturbed sleep patterns that interfere with restful sleep. Although fragmented sleep can be facilitated by a number of commercially-available sleep medications, many of those do not adequately improve sleep efficiency in the last hour of an 8-hour sleep period. As with treatments for terminal insomnia, if the dosage is increased sufficiently to improve sleep efficiency in the last hour of the sleep period, the patient may experience post-sleep sedation that interferes with normal activities.

Older patients are at particular risk for common side effects of conventional insomnia therapy, including next-day amnesia or memory loss, next-day sedation, and drug-drug interactions between sleep medications and other medications they may be taking.

Benzodiazepines and two of the most frequently used non-benzodiazepine agents in the treatment of insomnia, zolpidem and zaleplon, act through gamma-amino butyric acid (GABA) receptor inhibition and are considered to be Schedule IV drugs which have some risk of abuse and can lead to limited physical or psychological dependence. Two overt-the-counter antihistamines often used for treatment of insomnia, diphenhydramine and doxylamine, have substantial anticholinergic properties, with the potential to cause numerous side effects, especially among older patients.

Doxepin HCl is a tricyclic compound currently approved for treatment of depression. The recommended daily dose for the treatment of depression ranges from 75 mg to 300 mg. Doxepin, unlike most FDA approved products for the treatment of insomnia, is not a Schedule IV controlled substance.

U.S. Pat. Nos. 5,502,047 and 6,211,229, the entire contents of which are incorporated herein by reference, describe the use of doxepin for chronic and transient/short term insomnia, respectively, at dosages far below those used to treat depression. However, the mean half-life of doxepin is 17 hours, and the half-life of its major active metabolite, desmethyldoxepin, is 51 hours. Thus, when taken at the start of a sleep period, a majority of the drug or active metabolite should still be present in the body at the end of the sleep period. As a result, it would be expected that dosages of doxepin that are sufficient to address terminal insomnia or last-hour fragmented sleep in the elderly would also cause post-sleep sedation or other undesirable adverse effects.

The present invention describes the surprising ability of ultra-low dose doxepin (1-3 mg) to treat last-hour fragmented sleep and premature awakening in patients 65 years of age and older, without untoward side effects. Also, described is the use of doses between about 1 and 6 mg for the treatment of certain sleep conditions in a patient 65 years of age or older.

SUMMARY OF THE INVENTION

Some embodiments provide methods for treating insomnia in an elderly patient. In some embodiments, the methods include administering to a patient over the age of 65 an initial daily dosage of 1 mg doxepin, a pharmaceutically acceptable salt or a prodrug thereof; evaluating whether a desired improvement in sleep is achieved by the patient at the initial dosage; and if the desired improvement in sleep is not achieved, increasing the dosage of doxepin, the salt or the prodrug thereof incrementally until the desired dosage is achieved or until a maximum desired dosage is reached. In one aspect of the embodiment, the maximum desired dosage is selected from the group consisting of 1.5, 2, 2.5, and 3 milligrams. In some aspects, the initial dose can be 0.5 mg, for example.

Some embodiments provide methods for treating insomnia in an elderly individual at risk for amnesia or memory impairment resulting from sleep medication. In an embodiment, the methods include identifying an individual over the age of 65 that is at risk of or suffering from amnesia or memory impairment resulting from a sleep medication; administering to the individual an initial daily dosage of 1 milligram doxepin, a pharmaceutically acceptable salt or a prodrug thereof; evaluating whether a desired improvement in sleep or in avoidance of amnesia or memory impairment is achieved by the individual at the initial dosage; and if the desired improvement in sleep or in avoidance of amnesia or memory impairment is not achieved, increasing the dosage of doxepin, the salt, or the prodrug incrementally until the desired dosage is achieved or until a maximum desired dosage is reached. In one aspect of the embodiment, the maximum desired dosage is selected from the group consisting of 1.5, 2, 2.5, and 3 milligrams. In some aspects, the initial dose can be 0.5 mg, for example.

Some embodiments provide methods of decreasing wake time during sleep (WTDS) in a patient over the age of 65. In an embodiment, the methods include administering to the patient an initial daily dosage of 1 mg doxepin, a pharmaceutically acceptable salt or a prodrug thereof; evaluating whether a desired improvement in WTDS is achieved by the individual at the initial dosage; and if the desired improvement is not achieved, increasing the dosage of doxepin, the salt, or the prodrug incrementally until the desired dosage is achieved or until a maximum desired dosage is reached. In some embodiments, the maximum desired dosage is selected from the group consisting of 1.5, 2, 2.5, and 3 milligrams. In some aspects, the initial dose can be 0.5 mg, for example.

Some embodiments provide methods of decreasing latency to persistent sleep (LPS) in a patient over the age of 65. In some embodiments, the methods include administering to the patient an initial daily dosage of 3 mg doxepin, a pharmaceutically acceptable salt or a prodrug thereof. In some aspects, the initial dose can be 0.5 mg, 0.1, or 0.2 mg for example.

Some embodiments relate to methods for treating a sleep disorder, which methods can include identifying a patient over the age of 65 who is susceptible to one or more of the following side effects caused by sleep medication: nervous system side effects; psychiatric side effects; respiratory side effects; skin side effects; musculoskeletal side effects; and connective tissue side effects; and administering doxepin, pharmaceutically acceptable salts of the same, or prodrugs of the same to the patient. Preferably, the dosage can be about 1 mg to 6 mg. The identifying step can include identifying a patient who is susceptible to central nervous system side effects caused by sleep medication, and the central nervous system side effect can be, for example, at least one of somnolence, headache, dizziness, lethargy, and balance disorder. Also, the identifying step can include identifying a patient who is susceptible to psychiatric side effects caused by sleep medication. The psychiatric side effect can be, for example, at least one of anxiety, confusion, and abnormal dreams. In some aspects, the dose can be about 0.5 mg to about 10 mg, for example.

DETAILED DESCRIPTION OF THE INVENTION

Figure 1:
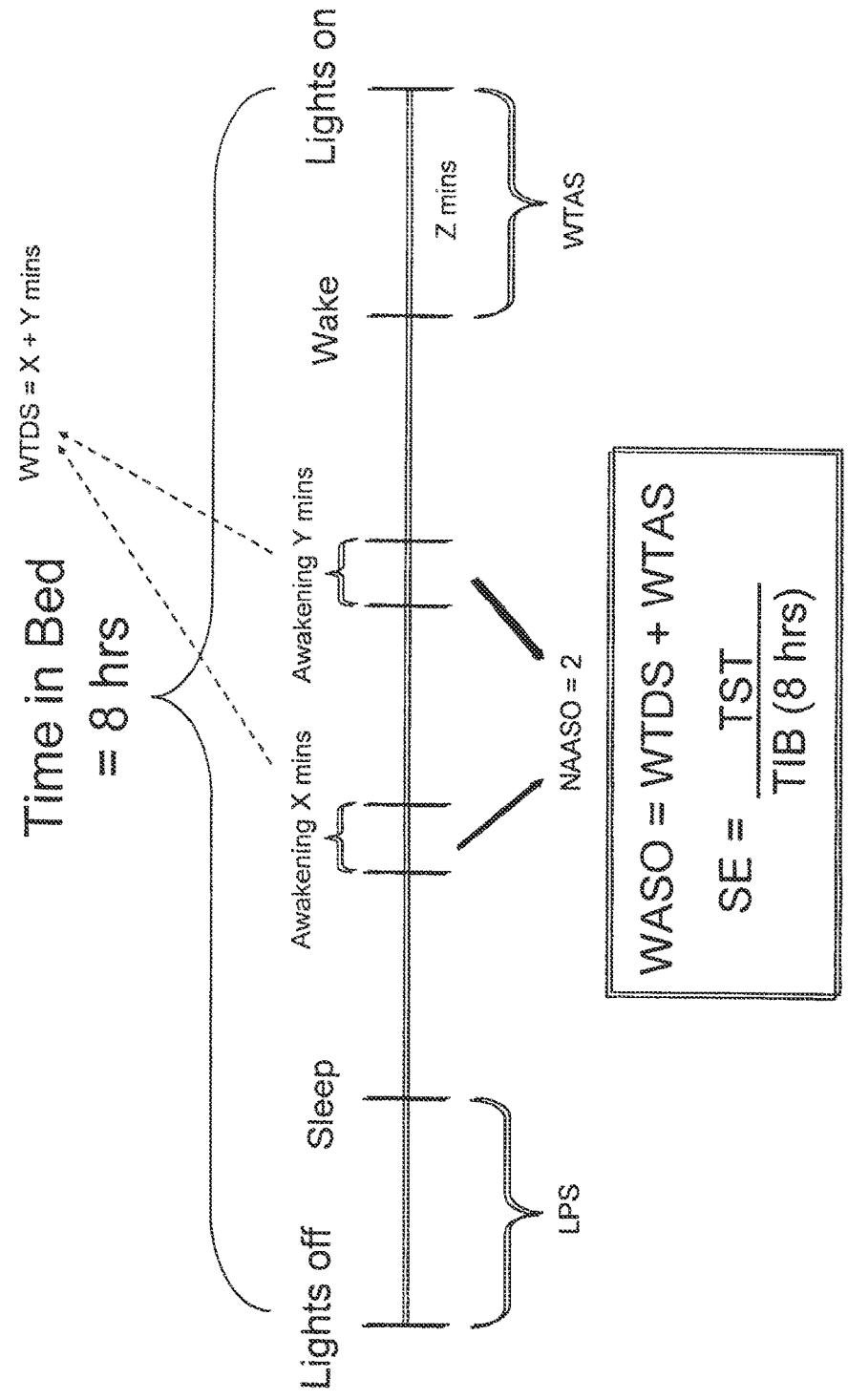
FIG. 1 illustrates the different parameters that can be analyzed using polysomnography.

One aspect of the invention relates to the ability of ultra-low-dose doxepin, pharmaceutically acceptable salts thereof or prodrugs thereof to treat fragmented sleep in the last hour of a sleep period, in particular an 8-hour sleep period and/or to treat premature final awakening (terminal insomnia) in the last hour of the sleep period in an elderly individual (65 years and older) by identifying an individual in need of such treatment, and providing an ultra-low dose of doxepin, a pharmaceutically acceptable salt thereof, or a prodrug thereof to the individual. Another aspect of the invention relates to treatment of elderly insomnia patients at risk for or desirous or reducing or avoiding post-sleep amnesia or memory loss resulting from sleep medication. It has been surprisingly discovered that an ultra-low dose of doxepin, particularly an initial dose of 1 mg, is more effective in patients 65 years and older than in younger adults. The term "ultra-low dose" refers to an initial daily dose of 1 mg and an ultimate daily dose between about 1 mg and 3 mg. In some embodiments, ultimate daily dosages of doxepin are about 1.5 mg, 2 mg or 2.5 mg. These ultra-low dosages have reduced side effects, are surprisingly effective, and have a relatively rapid onset. In some aspects, the final dose given or used to treat an elderly individual can be, for example, 4 mg, 5, mg or 6 mg. In some aspects, the initial dose used to treat an elderly individual can be 0.5 milligrams, for example.

In contrast to the treatment of primary insomnia in elderly patients in general and treatment of elderly individuals with the specific sleep disorders or side effect issues discussed above with an initial dose of 1 mg doxepin, it appears that the initial dose for treating non-elderly adult patients is more advantageously 3 mg or 6 mg. The efficacy of a 1 mg dosage for at least some insomnia treatments in elderly patients is believed to be surprising and is also believed to provide important advantages in treating insomnia in selected elderly patient populations.

Definitions

As used herein, the term "polysomnography" (PSG) refers a diagnostic test during which a number of physiologic variables are measured and recorded during sleep. Physiologic sensor leads are placed on the patient in order to record brain electrical activity, eye and jaw muscle movement, leg muscle movement, airflow, respiratory effort (chest and abdominal excursion), EKG and oxygen saturation. Information is gathered from all leads and fed into a computer and outputted as a series of waveform tracings which enable the technician to visualize the various waveforms, assign a score for the test, and assist in the diagnostic process. The primary efficacy variable, wake time during sleep (WTDS) and various secondary efficacy variables are all based on the PSG and are defined as follows.

"Wake Time During Sleep" (WTDS), typically expressed in minutes, is the number of wake events (epochs) after the onset of persistent sleep and prior to final awakening, divided by two. Each epoch is defined as a 30-second duration on the PSG recording.

"Wake Time After Sleep" (WTAS), typically expressed in minutes, is the number of epochs after the final awakening until the end of PSG recording (i.e., a wake epoch immediately prior to the end of the recording), divided by two. If the patient does not have a wake epoch immediately prior to the end of the recording, then WTAS is zero.

"Wake After Sleep Onset" (WASO) is the sum of WTDS and WTAS.

"sWASO" refers to subjective wake after sleep onset (WASO).

"Latency to Persistent Sleep" (LPS), typically expressed in minutes, is the number of epochs from the beginning of the PSG recording (lights-out) to the start of the first 20 consecutive non-wake epochs, divided by two.

"Total Sleep Time" (TST), typically expressed in minutes, is the number of non-wake epochs from the beginning of the PSG recording to the end of the recording, divided by two.

"sTST" refers to subjective total sleep time.

"Sleep Efficiency" (SE) is the TST divided by the time in bed (8 hours), multiplied by 100 and expressed as a percentage. This also can be divided into SE for each third-of-the-night of sleep, reflecting the SE for each 160 minute time interval across the night. Finally, SE can be measured for individual hours during the night or sleep period, for example the final hour of the sleep period.

"NAASO" refers to the number of awakenings after sleep onset.

"sNAASO" refers to subjective NAASO.

"LSO" refers to "latency to sleep onset, typically expressed in minutes.

The term "fragmented sleep" can refer to interrupted sleep over a measurement period or sleep period, for example the time a patient is awake during period of measurement. Fragmentation can occur as a result of multiple awakenings or one or more awakenings of a long duration.

The term "prodrug" refers to an agent that is converted into the active drug in vivo. Prodrugs are often useful because, in some situations, they may be easier to administer than the active drug. They may, for instance, be bioavailable by oral administration whereas the active drug is not. The prodrug may also have improved solubility in pharmaceutical compositions over the active drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "pharmaceutically acceptable salt" refers to an ionic form of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like.

Compounds

Doxepin:

Doxepin HCl is a tricyclic compound currently approved and available for treatment of depression and anxiety. Doxepin has the following structure:

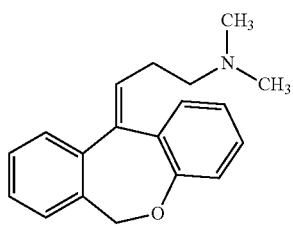 [SMILES: CN(C)CC/C=C1/c2ccccc2COc2ccccc21]

Doxepin belongs to a class of psychotherapeutic agents known as dibenzoxepin tricyclic compounds, and is currently approved and prescribed for use as an antidepressant to treat depression and anxiety. Doxepin has a well-established safety profile, having been prescribed for over 35 years.

Doxepin, unlike most FDA approved products for the treatment of insomnia, is not a Schedule IV controlled substance. U.S. Pat. Nos. 5,502,047 and 6,211,229, the entire contents of which are incorporated herein by reference, describe the use of doxepin for the treatment chronic and non-chronic (e.g., transient/short term) insomnias at dosages far below those used to treat depression.

It is contemplated that doxepin for use in the methods described herein can be obtained from any suitable source or made by any suitable method. As mentioned, doxepin is approved and available in higher doses (75-300 milligrams) for the treatment of depression and anxiety. Doxepin HCl is available commercially and may be obtained in capsule form from a number of sources. Doxepin is marketed under the commercial name SINEQUAN® and in generic form, and can be obtained in the United States generally from pharmacies in capsule form in amounts of 10, 25, 50, 75, 100 and 150 mg dosage, and in liquid concentrate form at 10 mg/mL. Doxepin HCl can be obtained from Plantex Ltd. Chemical Industries (Hakadar Street, Industrial Zone, P.O. Box 160, Netanya 42101, Israel), Sifavitor S.p.A. (Via Livelli 1—Frazione, Mairano, Italy), or from Dipharma S.p.A. (20021 Baranzate di Bollate, Milano, Italy). Also, doxepin is commercially available from PharmacyRx (NZ) (2820 1$^{st}$ Avenue, Castlegar, B.C., Canada) in capsule form in amounts of 10, 25, 50, 75, 100 and 150 mg. Furthermore, Doxepin HCl is available in capsule form in amounts of 10, 25, 50, 75, 100 and 150 mg and in a 10 mg/ml liquid concentrate from CVS Online Pharmacy Store (CVS.com).

Also, doxepin can be prepared according to the method described in U.S. Pat. No. 3,438,981, which is incorporated herein by reference in its entirety. As another illustration, doxepin can be prepared from 11-[3-(Dimethylamino)propyl]-6,11-dihydrodibenzo[b,e]-oxepin-11-ol as taught in U.S. Pat. No. 3,420,851, which is incorporated herein by reference in its entirety. It should be noted and understood that although many of the embodiments described herein specifically refer to "doxepin," other doxepin-related compounds can also be used, including, for example, pharmaceutically acceptable salts, prodrugs, metabolites, in-situ salts of doxepin formed after administration, and solid state forms, including polymorphs and hydrates.

Metabolites:

In addition, doxepin metabolites can be prepared and used. By way of illustration, some examples of metabolites of doxepin can include, but are not limited to, desmethyldoxepin, hydroxydoxepin, hydroxyl-N-desmethyldoxepin, doxepin, N-oxide, N-acetyl-N-desmethyldoxepin, N-desmethyl-N-formyldoxepin, quaternary ammonium-linked glucuronide, 2-O-glucuronyldoxepin, didesmethyldoxepin, 3-O-glucuronyldoxepin, or N-acetyldidesmethyldoxepin. The metabolites of doxepin can be obtained or made by any suitable method, including the methods described above for doxepin.

Desmethyldoxepin has the following structure:

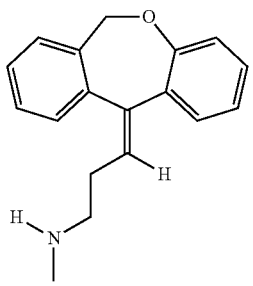 [SMILES: CNCC/C=C1\c2ccccc2COc2ccccc21]

Desmethyldoxepin is commercially available as a forensic standard. For example, it can be obtained from Cambridge Isotope Laboratories, Inc. (50 Frontage Road Andover, Mass.). Desmethyldoxepin for use in the methods discussed herein can be prepared by any suitable procedure. For example, desmethyldoxepin can be prepared from 3-methylaminopropyl triphenylphosphonium bromide hydrobomide and 6,11-dihydrodibenz(b,e)oxepin-11-one according to the method taught in U.S. Pat. No. 3,509,175, which is incorporated herein by reference in its entirety.

Hydroxydoxepin has the following structure:

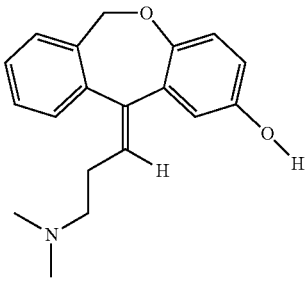 [SMILES: CN(C)CC/C=C1\c2ccccc2COc2ccc(O)cc21]

2-Hydroxydoxepin can be prepared by any suitable method, including as taught by Shu et al. (Drug Metabolism and Disposition (1990) 18:735-741), which is incorporated herein by reference in its entirety.

Hydroxyl-N-desmethyldoxepin has the following structure:

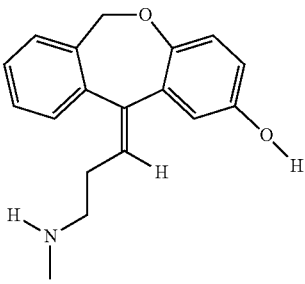 [SMILES: CNCC/C=C1\c2ccccc2COc2ccc(O)cc21]

2-Hydroxy-N-desmethyldoxepin can be prepared any suitable method.

Doxepin-N-oxide has the following structure:

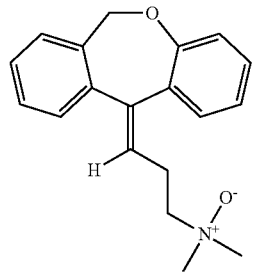 [SMILES: C[N+](C)([O-])CC/C=C1/c2ccccc2COc2ccccc21]

Doxepin N-oxide can be prepared by any suitable method. For example, doxepin N-oxide can be prepared as taught by Hobbs (*Biochem Pharmacol* (1969) 18:1941-1954), which is hereby incorporated by reference in its entirety.

N-acetyl-N-desmethyldoxepin has the following structure:

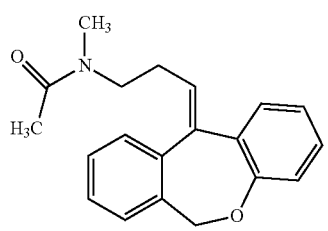

N-acetyl-N-desmethyldoxepin can be prepared by any suitable means. For example, (E)-N-acetyl-N-desmethyldoxepin has been produced in filamentous fungus incubated with doxepin as taught by Moody et al. (Drug Metabolism and Disposition (1999) 27:1157-1164), hereby incorporated by reference in its entirety.

N-desmethyl-N-formyldoxepin has the following structure:

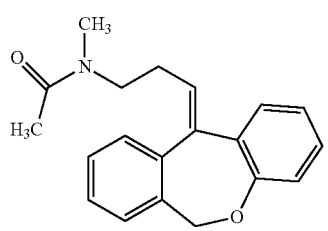 [SMILES: CC(=O)N(C)CC/C=C1\c2ccccc2COc2ccccc21]

N-desmethyl-N-formyldoxepin can be prepared by any suitable means. For example, (E)-N-desmethyl-N-formyldoxepin has been produced in filamentous fungus incubated with doxepin as taught by Moody et al. (Drug Metabolism and Disposition (1999) 27:1157-1164), hereby incorporated by reference in its entirety.

N-acetyldidesmethyldoxepin has the following structure:

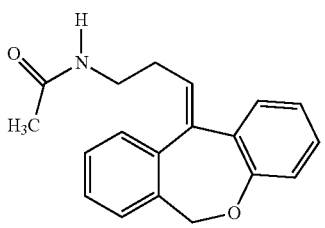

N-acetyldidesmethyldoxepin can be prepared by any suitable means. For example, (E)-N-acetyldidesmethyldoxepin has been produced in filamentous fungus incubated with doxepin as taught by Moody et al. (Drug Metabolism and Disposition (1999) 27:1157-1164), hereby incorporated by reference in its entirety.

Didesmethyldoxepin has the following structure:

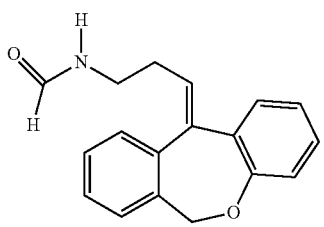 [SMILES: O=CNCC/C=C1\c2ccccc2COc2ccccc21]

Didesmethyldoxepin can be prepared by any suitable means. For example, (Z)- and (E)-didesmethyldoxepin have been isolated from plasma and cerebrospinal fluid of depressed patients taking doxepin, as taught by Deuschle et al. (Psychopharmacology (1997) 131:19-22), hereby incorporated by reference in its entirety.

3-O-glucuronyldoxepin has the following structure:

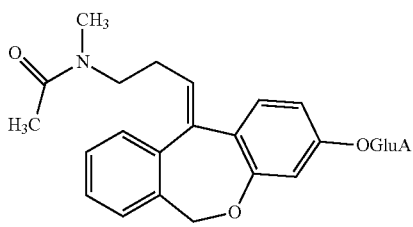

3-O-glucuronyldoxepin can be prepared by any suitable means. For example, (E)-3-O-glucuronyldoxepin has been isolated from the bile of rats given doxepin, as described by Shu el al. (Drug Metabolism and Disposition (1990) 18:1096-1099), hereby incorporated by reference in its entirety.

3-O-glucuronyldoxepin has the following structure:

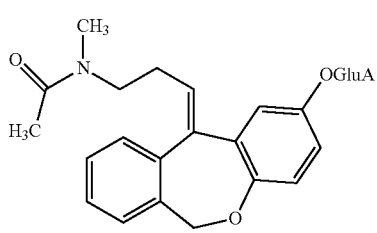

2-O-glucuronyldoxepin can be prepared by any suitable means. For example, (E)-2-O-glucuronyldoxepin has been isolated from the bile of rats given doxepin, and also in the urine of humans given doxepin, as described by Shu et al. (Drug Metabolism and Disposition (1990) 18:1096-1099), hereby incorporated by reference in its entirety.

Quaternary ammonium-linked glucuronide of doxepin (doxepin $N^+$-glucuronide) has the following structure:

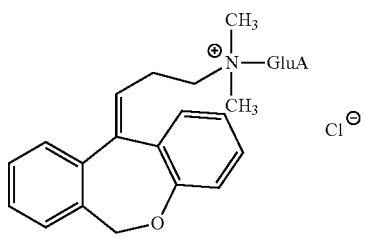

$N^+$-glucuronide can be obtained by any suitable means. For example, doxepin $N^+$-glucuronide can be prepared as taught by Luo et al. (Drug Metabolism and Disposition, (1991) 19:722-724), hereby incorporated by reference in its entirety.

Methods of Treating and Elderly Individual

In one embodiment of the present invention an individual who is at least 65 years of age who has insomnia is given an initial daily dosage of about 1 mg doxepin. It should be noted that in any of the methods described herein, a doxepin metabolite, prodrug or pharmaceutically acceptable salt thereof may be used in place of doxepin. If the desired improvement in sleep is not achieved, then the dosage may be incrementally increased until the desired dosage is achieved or until a maximum desired dosage is reached which may be, for example, 1.5 mg, 2 mg or 3 mg. Doxepin at the dosages described above demonstrated increased efficacy on objective and subjective sleep maintenance parameters in elderly individuals.

In another embodiment, an individual who is at least 65 years of age and is at risk for amnesia or memory impairment resulting from taking sleep medication can be treated. The methods of treatment can include, for example, identifying an individual over the age of 65 that is at risk or suffering irons amnesia or memory impairment resulting from a sleep medication; administering an initial dose of 1 mg doxepin to the individual; and evaluating whether a desired improvement in sleep is achieved, for example, a reduction in or lack of amnesia or memory impairment, for example, compared to the previous sleep medication. Further, if the desired improvement is not achieved, the methods can include the step of increasing the dosage. For example, the dosage can be increased to 1.5, 2, 2.5 or 3 milligrams. In some aspects, the dosage can be increased to 4.5 or 6 milligrams.

In another embodiment, an individual who is at least 65 years of age and who suffers from premature or early awakening or terminal insomnia can be treated. The methods of treatment can include, for example, identifying an individual over the age of 65 that is at suffers from premature early awakening; administering an initial dose of 1 mg doxepin to the individual; and evaluating whether a desired improvement in awakening is achieved, for example, a later final awakening. Also, if the desired improvement is not achieved, the methods can include the step of increasing the dosage. For example, the dosage can be increased to 1.5, 2, 2.5 or 3 milligrams. In some aspects, the dosage can be increased to 4, 5 or 6 milligrams.

Also, in another embodiment, an individual who is at least 65 years of age and who suffers from fragmented sleep in the $8^{th}$ hour of a sleep period can be treated. The methods of treatment can include, for example, identifying an individual over the age of 65 that is at suffers from fragmented sleep for the $8^{th}$ hour of a sleep period; administering an initial dose of 1 mg doxepin to the individual; and evaluating whether a desired improvement in sleep is achieved in the $8^{th}$ hour of the sleep period, for example, a reduction in the number and/or duration of awakenings. Also, if the desired improvement is not achieved, the methods can include the step of increasing the dosage. For example, the dosage can be increased to 1.5, 2, 2.5 or 3 milligrams. In some aspects, the dosage can be increased to 4, 5 or 6 milligrams.

In another embodiment, an individual who is at least 65 years of age and is in need of decreased WTDS is identified and is given an initial daily dosage of about 1 mg doxepin. If the desired improvement in sleep is not achieved, then the dosage may be incrementally increased until the desired dosage is achieved or until a maximum desired dosage is reached which may be, for example, 1.5 mg, 2 mg or 3 mg.

In another embodiment, an individual who is at least 65 years of age and is in need of decreased LPS is identified and is given an initial daily dosage of about 3 mg doxepin. If the desired improvement in sleep is not achieved, then the dosage may be incrementally increased until the desired dosage is achieved or until a maximum desired dosage is reached which may be, for example, 3.5, 4, 4.5, 5, 5.5 or 6 mg.

In another embodiment, an individual who is at least 65 years of age and is in need of decreased WTAS is identified and is given an initial daily dosage of about 1 mg or 3 mg doxepin. If the desired improvement in sleep is not achieved, then the dosage may be incrementally increased until the desired dosage is achieved or until a maximum desired dosage is reached which may be, for example, 3.5, 4, 4.5, 5 or 5.5 mg.

Some embodiments relate to methods for treating a sleep disorder, which methods can include identifying a patient over the age of 65 who is susceptible to one or more of the following side effects caused by sleep medication: nervous system side effects; psychiatric side effects; respiratory side effects; skin side effects; musculoskeletal side effects; and connective tissue side effects; and administering doxepin, pharmaceutically acceptable salts of the same, or prodrugs of the same to the patient. Preferably, the dosage can be about 1 mg to 6 mg. The identifying step can include identifying a patient who is susceptible to central nervous system side effects caused by sleep medication, and the central nervous system side effect can be, for example, at least one of somnolence, headache, dizziness, lethargy, and balance disorder. Also, the identifying step can include identifying a patient who is susceptible to psychiatric side effects caused by sleep medication. The psychiatric side effect can be, for example, at least one of anxiety, confusion, and abnormal dreams.

The methods described herein can be used to treat an individual that is 65 years of age or older, suffering from a sleep disorder, such as insomnia. The individual can suffer from a chronic insomnia or a non-chronic insomnia. For chronic (e.g., greater than 3-4 weeks) or non-chronic insomnias, a patient may suffer from difficulties in sleep onset, sleep maintenance (interruption of sleep during the night by periods of wakefulness), sleep duration, sleep efficiency, premature early-morning awakening, or a combination thereof. Also, the insomnia may be attributable to the concurrent use of other medication, for example. The non-chronic insomnia can be, for example, a short term insomnia or a transient insomnia. The chronic or non-chronic insomnia can be a primary insomnia or an insomnia that is secondary or attributable to another condition, for example a disease such as depression or chronic fatigue syndrome. In some aspects, the patient can one that is not suffering from an insomnia that is a component of a disease, or a patient can be treated that is otherwise healthy. As previously mentioned, the chronic or non-chronic insomnia can be a primary insomnia, that is, one that is not attributable to another mental disorder, a general medical condition, or a substance. In many cases, such conditions may be associated with a chronic insomnia and can include, but are not limited to, insomnia attributable to a diagnosable DSM-IV disorder, a disorder such as anxiety or depression, or a disturbance of the physiological sleep-awake system. In some aspects the insomnia can be non-chronic, or of short duration (e.g., less than 3-4 weeks). Examples of causes of such insomnia may be extrinsic or intrinsic and include, but are not limited to environmental sleep disorders as defined by the International Classification of Sleep Disorders (ICSD) such as inadequate sleep hygiene, altitude insomnia or adjustment sleep disorder. Also, short-term insomnia may also be caused by disturbances such as shift-work sleep disorder.

Administration of Doxepin

In performing the methods, doxepin, a pharmaceutically acceptable salt of doxepin, or prodrug of doxepin can be administered using any suitable route or method of delivery. Also, doxepin, a pharmaceutically acceptable salt or a prodrug thereof can be included and administered in a composition.

Suitable routes of administration include oral, buccal, sublingual, transdermal, rectal, topical, transmucosal, or intestinal administration; parenteral delivery, including intramuscular, subcutaneous, intravenous, intramedullary injections, as well as intrathecal, direct intraventricular, intraperitoneal intranasal, or intraocular injections.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Administration though oral pathways can be accomplished, for example, using a capsule, a tablet, a granule, a spray, a syrup, a liquid, powder, granules, pastes (e.g., for application to the tongue). Oral administration can be accomplished using fast-melt formulations, for example. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally, including sublingually, include for example, liquid solutions, powders, and suspensions in bulk or unit dosage forms. Also, the oral formulations can include, for example, pills, tablets, granules, sprays, syrups, pastes, powders, boluses, pre-measured ampules or syringes, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take any suitable form, for example, tablets or lozenges.

For topical administration, the compounds may be formulated for administration to the epidermis as ointments, gels, creams, pastes, salves, gels, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by infection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposome. Aqueous injection suspensions may contain substances which increase the viscosity of the suspension, such a sodium carboxymethyl cellulose, sorbitol, or dextran. Optionally, the suspension may also contain suitable stabilizers or agents which increase the solubility of the compounds to allow for the preparation of highly concentrated solutions.

In addition, any of the compounds and compositions described herein can also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Furthermore, any of the compounds and compositions described herein also can be formulated as a fast-melt preparation. The compounds and compositions can also be formulated and administered as a drip, a suppository, a salve, an ointment, an absorbable material such a transdermal patch, or the like.

One can also administer the compounds of the invention in sustained release forms or from sustained release drug delivery systems. A description of representative sustained release materials can be found in the incorporated materials in *Remington: The Science and Practice of Pharmacy* ($20^{th}$ ed, Lippincott Williams & Wilkens Publishers (2003)), which is incorporated herein by reference in its entirety.

A variety of techniques for formulation and administration can be found in *Remington: The Science and Practice of Pharmacy* ($20^{th}$ ed, Lippincott Williams & Wilkens Publishers (2003)), which is incorporated herein by reference in its entirety.

Compositions

As mentioned above, doxepin, pharmaceutically acceptable salts, and/or prodrugs of the same can be used alone or in combination with other substances, such as for example, other insomnia or sleep medications, or with other medications that treat a primary illness. The doxepin alone or in combination can be included as part of a composition. The compounds and compositions can include any suitable form of the compound for pharmaceutical delivery, as discussed in further detail herein.

The compositions and formulations disclosed herein also can include one or more pharmaceutically acceptable carrier materials or excipients. Such compositions can be prepared for storage and for subsequent administration. Acceptable carriers or diluents for therapeutic use are well known in the pharmaceutical art, and are described, for example, in the incorporated material of *Remington: The Science and Practice of Pharmacy* ($20^{th}$ ed, Lippincott Williams & Wilkens Publishers (2003)), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The pharmaceutical compositions can additionally include preservatives, solubilizers, stabilizers, wetting agents, emulsifiers, sweeteners, colorants, flavorings, buffers, coating agents, or antioxidants. Sterile compositions for injection can be formulated according to conventional pharmaceutical practice as described in the incorporated material in *Remington: The Science and Practice of Pharmacy* (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The compositions and formulations can include any other agents that provide improved transfer, delivery, tolerance, and the like. These compositions and formulations can include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Charman W N "Lipids, lipophilic drugs, and oral drug delivery-some emerging concepts." *J Pharm Sci* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Dosage

As mentioned above, in some embodiments the preferable dosage can be an ultra low dose between about 1 milligram and 3 milligrams. Preferably, the dosage can be about, 1 milligram, about 1.5 milligrams, about 2 milligrams, about 2.5 milligrams, or about 3 milligrams. It should be noted that in some embodiments the dosage can be about 4 milligrams, about 5 milligrams, about 6 milligrams. In some embodiments, the dosage can be between about 0.5 and 20 milligrams.

The selected dosage level can depend upon, for example, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. It will be understood, however, that the specific dose level for any particular patient can depend upon a variety of factors including the genetic makeup, body weight, general health, diet, time and route of administration, combination with other drugs and the particular condition being treated, and its severity. For the treatment of insomnia, preferably one dose is administered prior to bedtime.

Figure 2:
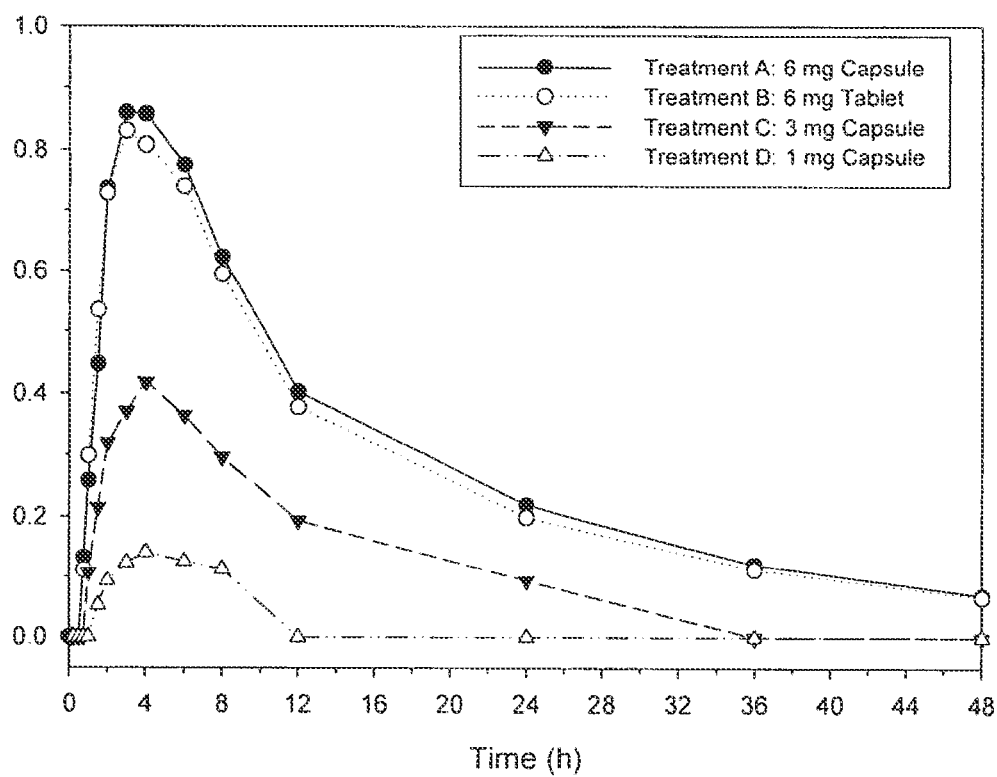
FIG. 2 is a graph showing the doxepin plasma profile concentration at various time points for 1 mg, 3 mg and 6 mg doxepin.

The selected dosage can also be determined by targeting a mean plasma concentration profile that has been associated with improvement in one or more PSG sleep variables including LPS, WASO, TST, SE, WTDS, or WTAS (FIG. 1). Examples of such plasma concentration profiles are shown in FIG. 2. The target plasma concentration profile may be achieved by any suitable route of administration including oral, buccal, sublingual, transdermal, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections using any suitable formulation.

EXAMPLES

Example 1

Study to Evaluate Sleep Maintenance Effects of Three Dose Levels of Doxepin Hydrochloride (HCl) Relative to Placebo in Elderly Patients with Primary Insomnia A randomized, multi-center, double-blind, placebo-controlled, four-period crossover, dose-response study was designed to assess the effects of doxepin (1 mg, 3 mg and 6 mg) compared with placebo in patients aged 65 years or older with primary sleep maintenance insomnia. Patients received a single-blind placebo for two consecutive nights during the PSG screening period, and double-blind study drug for two consecutive nights during each of the four treatment periods. Following each study drug administration, patients had 8 continuous hours of PSG recording in the sleep center. Patients were allowed to leave the sleep center during the day after each PSG assessment was complete. A 5- or 12-day study drug-free interval separated each PSG assessment visit. The duration of study participation per patient was approximately 7 to 11 weeks.

Patients who qualified for study entry, based on the screening PSG assessments, were randomized to a treatment sequence using a Latin square design. A final study visit was performed for patients either after completion of the four treatment periods or upon discontinuation from the study. Efficacy assessments were made at each visit and safety assessments were performed throughout the study.

Seventy-one patients were included in the per-protocol analysis set. The main inclusion criteria were male and/or female patients, aged 65 years or older, in good general health with at least a 3-month history of Diagnostic and Statistical Manual of Mental Disorders, fourth Edition (DSM-IV)-defined primary insomnia, reporting each of the following on four of seven nights prior to PSG screening: ≤6.5 hours of total sleep time (TST), ≥60 min of wakefulness after sleep onset (WASO) and ≥20 min of latency to sleep onset (LSO). Doxepin HCl 1 mg, 3 mg and 6 mg capsules, and placebo capsules, were provided as a single dose for oral administration.

The primary efficacy assessment was WTDS. Secondary efficacy assessments included WASO, SE, TST, LPS, and WTAS, All objective efficacy assessments were performed on Night 1 and Night 2 of each treatment period.

Efficacy analyses used the per-protocol (PP; the primary analysis set) sets. The PP analysis set included all patients who did not have important protocol derivations that would likely have effected the evaluation of efficacy, and who provided WTDS data from each of the four treatment periods. The primary and secondary efficacy analyses were based on the PP analysis set.

Within each treatment period, the average of the two data points was used for analysis, if applicable. The primary efficacy variable, WTDS, as well as the secondary objective and subjective efficacy parameters were analyzed using an analysis of variance (ANOVA) model with terms for sequence, patient within sequence, treatment and period. Pairwise comparisons of each active treatment versus placebo were performed using Dunnett's test.

All randomized patients who received at least one dose of double-blind study medication were included in the safety analyses, which were based on observed data.

Efficacy Results

Primary

WTDS exhibited a statistically significant decrease at the doxepin 1 mg (p=0.0001), 3 mg (p<0.0001) and 6 mg (p<0.0001) dose levels compared with placebo in the PP analysis set. The observed mean values (±SD) were: placebo 86.0 (38.15); doxepin 1 mg 70.1 (32.78); doxepin 3 mg 66.4 (31.56) and doxepin 6 mg 60.2 (28.00). The results using the ITT analysis set were consistent with those from the PP analysis set.

Secondary

The secondary PSG efficacy assessments are summarized in Table 1. WASO exhibited a statistically significant decrease at the doxepin 1 mg (p<0.0001), 3 mg (p<0.0001), and 6 mg (p<0.0001) dose levels compared to placebo. SE exhibited statistically significant increases at all three dose levels of doxepin (1 mg, p<0.0001; 3 mg, p<0.0001; 6 mg, p<0.0001) compared to placebo. TST exhibited statistically significant increases at all three dose levels of doxepin (1 mg, p<0.0001; 3 mg, p<0.0001; 6 mg, p<0.0001) compared to placebo. LPS was numerically decreased at the 3 mg and 6 mg dose levels. There were no significant differences at any dose level of doxepin compared with placebo for NAASO. WTAS exhibited a statistically significant decrease at the doxepin 3 mg (p=0.0264) and 6 mg (p=0.0008) dose levels and numerically reduced at the doxepin 1 mg dose level, all compared to placebo.

TABLE 1

Secondary PSG Efficacy Assessments: Per-Protocol Analysis Set

| Parameter | Placebo Mean | Doxepin 1 mg | | Doxepin 3 mg | | Doxepin 6 mg | |
|---|---|---|---|---|---|---|---|
| | | Mean | P-value[1] | Mean | P-value[1] | Mean | P-value[1] |
| Per-Protocol (N = 71) | | | | | | | |
| WASO (minutes) | 99.0 | 80.5 | <0.0001 | 72.3 | <0.0001 | 65.2 | <0.0001 |
| SE (percent) | 74.9 | 78.5 | <0.0001 | 81.0 | <0.0001 | 82.8 | <0.0001 |
| TST (minutes) | 359.4 | 376.8 | <0.0001 | 388.8 | <0.0001 | 397.4 | <0.0001 |
| LPS (minutes)[2] | 27.1 | 28.3 | 0.9896 | 23.7 | 0.0964 | 22.4 | 0.1959 |
| NAASO | 12.0 | 12.3 | 0.7689 | 12.8 | 0.2801 | 12.5 | 0.2742 |
| WTAS (minutes) | 13.0 | 10.4 | 0.5546 | 5.9 | 0.0264 | 5.0 | 0.0008 |
| WTDS | 86.0 | 70.1 | 0.0001 | 66.4 | <0.0001 | 60.2 | <0.0001 |

[1]P-value comparing each active treatment versus placebo using Dunnett's test
[2]LPS data were log-transformed prior to analysis Thus, 1 mg, 3 mg and 6 mg doxepin demonstrated efficacy on objective and subjective sleep maintenance parameters in elderly patients (65 years of age and older) with primary sleep maintenance insomnia, which appeared to be dose-related. Efficacy in delaying early morning awakenings (terminal insomnia) was also demonstrated for doxepin 1 mg, 3 mg and 6 mg as evidenced by statistically significant reductions in WTAS at the doxepin 3 mg and 6 mg dose levels and numerical reductions at the doxepin 1 mg dose level, all compared to placebo. As demonstrated by Table 2, all doxepin doses were well tolerated, and demonstrated an adverse effect profile similar to placebo with no reports of anti-cholinergic effects or amnesia/memory impairment; no drug-related serious adverse events; and no clinically meaningful changes to vitals, physical exams, electrocardiogram, or safety labs. No meaningful changes to sleep architecture were observed. There were no significant effects observed on next-day residual sedation.

Table 2 summarizes the adverse events as reported by the elderly patients. The adverse events are arranged by system organ class.

TABLE 2

Adverse Events by MedDRA System Organ Class
Safety Analysis Set

| System Organ Class/Preferred Term | Placebo (N = 73) Number of Patients | Number of Events | Doxepin HCl 1 mg (N = 74) Number of Patients | Number of Events | Doxepin HCl 3 mg (N = 75) Number of Patients | Number of Events | Doxepin HCl 6 mg (N = 74) Number of Patients | Number of Events |
|---|---|---|---|---|---|---|---|---|
| Patients Reporting at Least One Adverse Event | 7 (10%) | 8 | 9 (12%) | 10 | 6 (8%) | 8 | 5 (7%) | 6 |
| NERVOUS SYSTEM DISORDERS | 3 (4%) | 3 | 2 (3%) | 2 | 2 (3%) | 2 | 1 (1%) | 1 |
| SOMNOLENCE | 0 (0%) | 0 | 1 (1%) | 1 | 1 (1%) | 1 | 1 (1%) | 1 |
| HEADACHE | 2 (3%) | 2 | 0 (0%) | 0 | 0 (0%) | 0 | 0 (0%) | 0 |
| BALANCE DISORDER | 1 (1%) | 1 | 0 (0%) | 0 | 0 (0%) | 0 | 0 (0%) | 0 |
| DIZZINESS | 0 (0%) | 0 | 0 (0%) | 0 | 1 (1%) | 1 | 0 (0%) | 0 |
| LETHARGY | 0 (0%) | 0 | 1 (1%) | 1 | 0 (0%) | 0 | 0 (0%) | 0 |
| PSYCHIATRIC DISORDERS | 2 (3%) | 2 | 1 (1%) | 1 | 1 (1%) | 1 | 1 (1%) | 1 |
| ANXIETY | 1 (1%) | 1 | 1 (1%) | 1 | 1 (1%) | 1 | 0 (0%) | 0 |
| ABNORMAL DREAMS | 1 (1%) | 1 | 0 (0%) | 0 | 0 (0%) | 0 | 0 (0%) | 0 |
| CONFUSIONAL STATE | 0 (0%) | 0 | 0 (0%) | 0 | 0 (0%) | 0 | 1 (1%) | 1 |
| INFECTIONS AND INFESTATIONS | 0 (0%) | 0 | 3 (4%) | 3 | 0 (0%) | 0 | 1 (1%) | 1 |
| CYSTITIS | 0 (0%) | 0 | 1 (1%) | 1 | 0 (0%) | 0 | 0 (0%) | 0 |
| DENTAL CARIES | 0 (0%) | 0 | 0 (0%) | 0 | 0 (0%) | 0 | 1 (1%) | 1 |
| FUNGAL INFECTION | 0 (0%) | 0 | 1 (1%) | 1 | 0 (0%) | 0 | 0 (0%) | 0 |
| NASOPHARYNGITIS | 0 (0%) | 0 | 1 (1%) | 1 | 0 (0%) | 0 | 0 (0%) | 0 |
| INVESTIGATIONS | 2 (3%) | 3 | 1 (1%) | 1 | 0 (0%) | 0 | 1 (1%) | 1 |
| ELECTROCARDIOGRAM ST-T SEGMENT ABNORMAL | 1 (1%) | 1 | 1 (1%) | 1 | 0 (0%) | 0 | 0 (0%) | 0 |
| QRS AXIS ABNORMAL | 1 (1%) | 2 | 0 (0%) | 0 | 0 (0%) | 0 | 1 (1%) | 1 |
| EYE DISORDERS | 0 (0%) | 0 | 1 (1%) | 1 | 1 (1%) | 1 | 0 (0%) | 0 |
| VISION BLURRED | 0 (0%) | 0 | 1 (1%) | 1 | 1 (1%) | 1 | 0 (0%) | 0 |
| GENERAL DISORDERS AND ADMINISTRATION SITE CONDITIONS | 0 (0%) | 0 | 1 (1%) | 1 | 1 (1%) | 2 | 0 (0%) | 0 |
| ASTHENIA | 0 (0%) | 0 | 0 (0%) | 0 | 1 (1%) | 1 | 0 (0%) | 0 |
| FATIGUE | 0 (0%) | 0 | 0 (0%) | 0 | 1 (1%) | 1 | 0 (0%) | 0 |
| NON-CARDIAC CHEST PAIN | 0 (0%) | 0 | 1 (1%) | 1 | 0 (0%) | 0 | 0 (0%) | 0 |
| RESPIRATORY, THORACIC AND MEDIASTINAL DISORDERS | 0 (0%) | 0 | 1 (1%) | 1 | 1 (1%) | 1 | 0 (0%) | 0 |
| PHARYNGOLARYNGEAL PAIN | 0 (0%) | 0 | 0 (0%) | 0 | 1 (1%) | 1 | 0 (0%) | 0 |
| WHEEZING | 0 (0%) | 0 | 1 (1%) | 1 | 0 (0%) | 0 | 0 (0%) | 0 |
| MUSCULOSKELETAL AND CONNECTIVE TISSUE DISORDERS | 0 (0%) | 0 | 0 (0%) | 0 | 0 (0%) | 0 | 1 (1%) | 2 |
| SENSATION OF HEAVINESS | 0 (0%) | 0 | 0 (0%) | 0 | 0 (0%) | 0 | 1 (1%) | 2 |
| SKIN AND SUBCUTANEOUS TISSUE DISORDERS | 0 (0%) | 0 | 0 (0%) | 0 | 1 (1%) | 1 | 0 (0%) | 0 |
| SKIN IRRITATION | 0 (0%) | 0 | 0 (0%) | 0 | 1 (1%) | 1 | 0 (0%) | 0 |

At each level of summation (overall, system organ class, preferred term), patients reporting more than one adverse event per treatment are counted only once. Each event is assigned to the most recent treatment received prior to onset.

The patients report subjected data, which were consistent with the PSG data. Subjective WASO (sWASO) was statistically significantly decreased at all doxepin dose levels (1 mg, p=0.0297; 3 mg, p=0.0144; 6 mg, p=0.0074) compared with placebo. sTST was statistically significantly increased at all doxepin dose levels (1 mg, p=0.0182; 3 mg, p=0.0005; 6 mg, p<0.0001) compared with placebo. Latency to sleep onset (LSO) was statistically significantly decreased at the doxepin 6 mg dose level (p=0.0174), and numerically decreased at the 1 mg and 3 mg dose levels compared with placebo. Sleep quality was statistically significantly increased at all doxepin dose levels (1 mg, p=0.0357; 3 mg, p=0.0019; 6 mg, p=0.0047) compared with placebo. The results are summarized in Table 3.

TABLE 3

Subjective Sleep Data

| Parameter | Placebo (n = 71) | Doxepin 1 mg (n = 71) | Doxepin 3 mg (n = 71) | Doxepin 6 mg (n = 71) |
|---|---|---|---|---|
| sWASO: | | | | |
| Mean (SD) | 89.6 (60.7) | 74.3 (55.2) | 72.2 (56.4) | 71.5 (57.4) |
| p-value | | 0.0297 | 0.0144 | 0.0074 |
| sTST: | | | | |
| Mean (SD) | 339.1 (71.6) | 355.7 (63.1) | 362.4 (64.3) | 369.4 (65.3) |
| p-value | | 0.0182 | 0.0005 | <0.0001 |
| LSO: | | | | |
| Mean (SD) | 45.8 (35.9) | 42.3 (32.1) | 42.4 (40.1) | 33.9 (24.8) |
| p-value | | 0.9961 | 0.3172 | 0.0174 |

TABLE 3-continued

Subjective Sleep Data

| Parameter | Placebo (n = 71) | Doxepin 1 mg (n = 71) | Doxepin 3 mg (n = 71) | Doxepin 6 mg (n = 71) |
|---|---|---|---|---|
| sNAASO: | | | | |
| Mean (SD) | 3.2 (1.6) | 3.2 (2.1) | 2.9 (1.7) | 3.0 (1.4) |
| p-value | | 0.9985 | 0.3224 | 0.4080 |
| Sleep Quality: | | | | |
| Mean (SD) | 0.5 (1.0) | 0.8 (1.0) | 0.9 (1.0) | 0.8 (1.0) |
| p-value | | 0.0357 | 0.0019 | 0.0047 |

Example 2

A Phase III, Randomized, Double-Bind, Placebo-Controlled, Parallel-Group, Multicenter Study to Assess the Long Term Efficacy and Safety of Doxepin HCl in Primary Elderly Insomnia Patients with Sleep Maintenance Difficulties A phase III, randomized, double-blind, placebo-controlled, parallel-group, multicenter study was conducted to assess the long term efficacy and safety of two dose levels of doxepin HCl, 1 mg and 3 mg, in primary elderly insomnia patients with sleep maintenance difficulties.

Subjects were females and males, 65 years of age or older, with at least a 3-month history of primary insomnia (as defined in the Diagnostic and Statistical Manual of Mental Disorders, Fourth Edition, Text Revision), who reported experiencing at least 60 minutes of Wake After Sleep Onset (WASO), at least 30 minutes of Latency to Sleep Onset (LSO), and no more than 6.5 hours of Total Sleep Time (TST) on at least 4 of 7 consecutive nights prior to PSG Screening.

Doxepin 1 mg tablets or 3 mg tablets (lot number 3044567) were administered as a single oral dose for 85 consecutive nights during the 12-week Double-blind Treatment Period.

Primary Efficacy Variable: The primary efficacy variable was WASO on Night 1.

Additional PSG Variables: Additional efficacy variables assessed on each PSG recording night during the Double-blind Treatment Period were WASO (Night 15, Night 29, Night 57, and Night 85); WTDS; TST; Sleep Efficiency (SE) overall, by third of the night, the last quarter of the night, and hour of the night; LPS; Latency to Stage 2 Sleep; Number of Awakenings After Sleep Onset (NAASO) overall and by hour; Total Wake Time (TWT) overall and by hour; Wake Time After Sleep (WTAS); and sleep architecture (including percentage and minutes of Stage 1, 2, and 3-4 sleep; percentage and minutes of rapid eye movement [REM] and non-REM sleep; and Latency to REM Sleep.)

Subjective Variables: Subjective efficacy variables were subjective TST (sTST), subjective WASO (sWASO), LSO, subjective NAASO (sNAASO), and sleep quality. These variable were assessed using a questionnaire completed in the morning following each PSG recording night. Drowsiness, ability to function, and total nap time during the day were assessed using an evening questionnaire completed prior to PSG recording at Nights −6, −5, 1, 15, 29, 57, and 85. Other secondary subjective efficacy variables included the 2-item Clinical Global Impressions (CGI) scale for severity of illness and therapeutic effect completed by a clinician; the 5-item CGI scale pertaining to therapeutic effect completed by the subject; the Insomnia Severity Index (ISI) completed by the subject, and a subjective assessment of sTST, LSO, and sleep quality collected through the IVRS.

Of the 240 randomized subjects, 214 (89%) completed the study. Early termination rates and baseline characteristics were comparable across treatment groups. Subjects were female (65%) and male (35%). The mean age was 71.4 years. Subjects were White (80%), Black/African American (9%), Hispanic (9), Asian (1%), and Other (1%).

Efficacy Results:

Primary Efficacy Variable (WASO on Night 1) Using the ITT Analysis Set

The WASO results are shown in Table 4. Mean WASO on Night 1 was statistically significantly decreased following administration of doxepin 1 mg and 3 mg compared with placebo. The least-square (LS) mean WASO was shorter for the doxepin 1 mg and 3 mg groups by 17.8 minutes and 33.8 minutes, respectively, compared with the placebo group. Additionally, in the doxepin 3 mg group the LS mean WASO was statistically significantly decreased compared with placebo at each assessment through 85 nights of treatment. Improvement in WASO on Night 1 was independent of sex.

TABLE 4

WASO at Baseline, Night 1 and Night 85: ITT Analysis Set

| | WASO (minutes) | | |
|---|---|---|---|
| | Placebo (N = 81) | Doxepin 1 mg (N = 77) | Doxepin 3 mg (N = 82) |
| Baseline (mean of Nights-6 and -5) | 119.5 (37.67) | 120.1 (34.97) | 117.9 (28.15) |
| Night 1 (Primary Efficacy Variable) | n = 81 | n = 77 | n = 82 |
| Mean (SD) | 108.9 (46.01) | 91.8 (47.09) | 74.5 (37.88) |
| Diff. of LS Mean (Std. Err.) | | −17.8 (6.32) | −33.8 (6.23) |
| p-value | | p = 0.0053 | p < 0.0001 |
| Night 85 | n = 70 | n = 69 | n = 74 |
| Mean (SD) | 109.2 (50.83) | 97.0 (44.18) | 75.7 (37.55) |
| Diff. of LS Mean (Std. Err.) | | −14.6 (6.80) | −33.2 (6.70) |
| p-value | | p = 0.0330 | p < 0.0001 |

SD = standard deviation.
p-value comparing each active treatment versus placebo from ANCOVA model that included main effects for treatment and center with the baseline value as a covariate, using a linear contrast.

Additional Objective Variables

There were statistically significant improvements at multiple timepoints on multiple PSG measures of sleep maintenance (including TST, SE overall, WTDS, and TWT overall) and PSG measures of prevention of early morning awakenings (including WTAS. These results are summarized in Table 5.

TABLE 5

Additional Key Objective PSG Efficacy Variables on
Night 1 and Night 85: ITT Analysis Set

| PSG Variable | Placebo (N = 81) | Doxepin 1 mg (N = 77) | Doxepin 3 mg (N = 82) |
|---|---|---|---|
| TST (minutes) | | | |
| Baseline | 320.6 (40.25) | 322.4 (39.93) | 326.9 (33.16) |
| Night 1 | 339.7 (54.35) | 359.1 (53.05) | 382.9 (44.23) |
|  |  | p = 0.0119 | p < 0.0001 |
| Night 85 | 343.7 (57.72) | 360.5 (47.17) | 373.7 (42.24) |
|  |  | p = 0.0257 | p = 0.0007 |
| SE Overall (%) | | | |
| Baseline | 66.8 (8.39) | 67.2 (8.32) | 68.1 (6.91) |
| Night 1 | 70.8 (11.32) | 74.8 (11.05) | 79.8 (9.21) |
|  |  | p = 0.0119 | p < 0.0001 |
| Night 85 | 71.6 (12.03) | 75.1 (9.83) | 77.9 (8.80) |
|  |  | p = 0.0257 | p = 0.0007 |
| WTAS (minutes) | | | |
| Baseline | 10.1 (14.99) | 9.7 (16.31) | 9.8 (15.27) |
| Night 1 | 10.7 (22.63) | 8.9 (18.84) | 4.7 (14.61) |
|  |  | p = 0.6405 | p = 0.0556 |
| Night 85 | 12.2 (21.73) | 10.8 (21.78) | 5.4 (13.20) |
|  |  | p = 0.6514 | p = 0.0284 |
| LPS (minutes)[1] | | | |
| Baseline | 49.0 (27.34) | 45.4 (25.25) | 41.9 (22.65) |
| Night 1 | 39.6 (29.28) | 38.8 (29.58) | 28.6 (20.53) |
|  |  | p = 0.5733 | p = 0.1079 |
| Night 85 | 34.9 (32.96) | 29.0 (26.45) | 37.5 (32.74) |
|  |  | p = 0.6493 | p = 0.0286 |

Data presented are mean (SD).
p-value comparing each active treatment versus placebo was determined from an ANCOVA model that included main effects for treatment and center with the baseline value as a covariate, using a linear contrast.
[1]Analysis performed on log-transformed data.

Clinical Global Impressions (CGI) ns (CGI) consist of two questions addressed to the clinician relating to the severity of illness and therapeutic effect of the study drug and five questions addressed to the patient relating to the therapeutic effect of the drug.

CGI Clinician-rated: There were statistically significant improvements in mean CGI severity of illness and therapeutic effect scores at Night 85 in both doxepin treatment groups compared with placebo. Notably, the mean CGI severity of illness score decreased by one global category (a mean change from moderate severity at baseline to mild severity at Night 85) in both doxepin groups. Similarly, the mean CGI therapeutic effect score was improved by one global category in both doxepin groups. These improvements were not observed in the placebo group for either assessment.

CGI Subject-rated: There were statistically significant improvements in CGI therapeutic effect scores compared with placebo in each doxepin group at each visit for one or more parameters. After 85 nights of treatment, there were statistically significant improvements for both doxepin groups compared with placebo on all five parameters of the subject-rated CGI scale of therapeutic effect.

Doxepin (1 mg and 3 mg) administered 30 minutes before each subject's bedtime for up to 85 consecutive nights was safe and well-tolerated. Safety profiles were comparable across the three treatment groups. There were no reported deaths during the study or within 30 days following administration of the last dose of study medication.

There were no clinically relevant effects on sleep architecture. Sleep stages generally were preserved.

There was no apparent evidence of next-day drowsiness based on mean scores from the DSST, SCT, and VAS for sleepiness, or impairment of daytime functioning or daytime drowsiness based on the evening questionnaire.

Approximately 40% of subjects in the doxepin 1 mg group and 38% of subjects in the doxepin 3 mg group reported a TEAE, compared with 52% of subjects in the placebo group. Table 6 summarizes all TEAEs experienced by greater than or equal to 2% of all subjects.

Overall, both the 1 mg and 3 mg doses demonstrated improvement compared to placebo. Both doxepin dose levels were safe and well-tolerated with no apparent dose-related effects on safety. These data support the use of doxepin 1 mg and 3 mg in elderly subjects with chronic insomnia.

TABLE 6

TEAEs Experienced by Greater than or Equal to 2 Percent of Subjects in any Treatment Group: Safety Analysis Set

| MedDRA System Organ Class/Preferred Term | Placebo (N = 81) | Doxepin 1 mg (N = 77) | Doxepin 3 mg (N = 82) |
|---|---|---|---|
| Subject with any TEAE | 42 (52%) | 31 (40%) | 31 (38%) |
| Infections and Infestations | 11 (14%) | 12 (16%) | 11 (13%) |
| Gastroenteritis | 0 (0%) | 0 (0%) | 3 (4%) |
| Nasopharyngitis | 1 (1%) | 1 (1%) | 2 (2%) |
| Bronchitis | 2 (2%) | 1 (1%) | 1 (1%) |
| Upper respiratory tract infection | 1 (1%) | 2 (3%) | 1 (1%) |
| Sinusitis | 1 (1%) | 3 (4%) | 0 (0%) |
| Urinary tract infection | 2 (2%) | 2 (3%) | 0 (0%) |
| Nervous System Disorders | 16 (20%) | 6 (8%) | 9 (11%) |
| Headache | 11 (14%) | 2 (3%) | 5 (6%) |
| Dizziness | 2 (2%) | 0 (0%) | 2 (2%) |
| Somnolence | 4 (5%) | 4 (5%) | 2 (2%) |
| Gastrointestinal Disorders | 10 (12%) | 4 (5%) | 5 (6%) |
| Dry mouth | 2 (2%) | 1 (1%) | 2 (2%) |
| Stomach discomfort | 0 (0%) | 0 (0%) | 2 (2%) |
| Diarrhoea | 2 (2%) | 2 (3%) | 0 (0%) |
| Nausea | 2 (2%) | 0 (0%) | 0 (0%) |
| Vascular Disorders | 0 (0%) | 2 (3%) | 5 (6%) |
| Hypertension | 0 (0%) | 1 (1%) | 3 (4%) |
| Injury, Poisoning and Procedural Complications | 5 (6%) | 1 (1%) | 4 (5%) |
| Fall | 0 (0%) | 0 (0%) | 2 (2%) |
| Joint sprain | 1 (1%) | 0 (0%) | 2 (2%) |
| Respiratory, Thoracic and Mediastinal Disorders | 5 (6%) | 2 (3%) | 4 (5%) |
| Pharyngolaryngeal pain | 2 (2%) | 0 (0%) | 0 (0%) |
| Psychiatric Disorders[1] | 1 (1%) | 1 (1%) | 2 (2%) |
| Musculoskeletal and Connective Tissue Disorders | 3 (4%) | 1 (1%) | 2 (2%) |
| Back pain | 1 (1%) | 0 (0%) | 2 (2%) |

[1]Psychiatric Disorders SOC included because of its relevance to sleep disorders. No individual preferred terms within this SOC were reported by ≥2 subjects in any treatment group.

Example 3

Study to Evaluate Sleep Maintenance Effects of Three Dose Levels of Doxepin Hydrochloride (HCl) Relative to Placebo in Adult Patients (Ages 18-64) with Primary Insomnia A randomized, multi-center, double-blind, placebo-controlled, four-period crossover, dose-response study was designed to assess the effects of doxepin (1 mg, 3 mg and 6 mg) compared with placebo in patients with primary sleep maintenance insomnia.

Patients received a single-blind placebo for two consecutive nights during the PSG screening period, and double-blind study drug for two consecutive nights during each of the four treatment periods. Following each study drug administration, patients had 8 continuous hours of PSG recording in the sleep center. Patients were allowed to leave the sleep center during the day after each PSG assessment was complete. A 5- or 12-day study drug-free interval separated each PSG assessment visit.

Patients who qualified for study entry, based on the screening PSG assessments, were randomized to a treatment sequence using a Latin square design. A final study visit was performed for patients either after completion of the four treatment periods or upon discontinuation from the study. Efficacy assessments were made at each visit and safety assessments were performed throughout the study.

Sixty-one patients were included in the per-protocol analysis set. The main inclusion criteria were male and/or female patients, aged 18 to 64 years, in good general health with at least a 3-month history of DSM-IV-defined primary insomnia, reporting each of the following on four of seven nights prior to PSG screening: ≤6.5 hours of total sleep time (TST), ≥60 min of WASO and ≥20 min of LSO. Doxepin HCl 1 mg, 3 mg and 6 mg capsules, and placebo capsules, were provided as a single dose for oral administration.

The primary and secondary efficacy assessments were as described above in Example 1. All objective efficacy assessments were performed on Night 1 and Night 2.

Efficacy Results
Primary

WTDS exhibited a statistically significant decrease at the doxepin 3 mg (p<0.0001) and 6 mg (p=0.0002) dose levels compared with placebo. WTDS was numerically, but not significantly decreased at the doxepin 1 mg dose level. The observed mean values (±SD) were: placebo 51.9 (42.25); doxepin 1 mg 43.2 (28.2); doxepin 3 mg 33.4 (21.87) and doxepin 6 mg 35.3 (25.17).

Secondary

The secondary PSG efficacy assessments are summarized in Table 7. WASO exhibited a statistically significant decrease at the doxepin 1 mg (p=0.0130), 3 mg (p<0.0001), and 6 mg (p<0.0001) dose levels compared to placebo. SE exhibited statistically significant increases at all three dose levels of doxepin (1 mg, p=0.0004; 3 mg, p<0.0001; 6 mg, p<0.0001) compared to placebo. TST exhibited statistically significant increases at all three dose levels of doxepin (1 mg, p=0.0004; 3 mg, p<0.0001; 6 mg, p<0.0001) compared to placebo. Although there were no significant differences between doxepin and placebo at any dose level for LPS, LPS was numerically decreased, most notably at the 6 mg dose level. There were no significant differences at any dose level of doxepin compared with placebo for NAASO. WTAS exhibited a statistically significant decrease at the doxepin 6 mg dose level (p=0.0105) compared to placebo.

TABLE 7

Secondary PSG Efficacy Assessments: Per-Protocol Analysis Set

| Parameter | Placebo Mean | Doxepin 1 mg Mean | Doxepin 1 mg P-value[1] | Doxepin 3 mg Mean | Doxepin 3 mg P-value[1] | Doxepin 6 mg Mean | Doxepin 6 mg P-value[1] |
|---|---|---|---|---|---|---|---|
| | | | Per-Protocol (N = 61) | | | | |
| WASO (minutes) | 62.1 | 47.3 | 0.0130 | 38.6 | <0.0001 | 38.8 | <0.0001 |
| SE (percent) | 80.7 | 84.7 | 0.0004 | 86.5 | <0.0001 | 86.9 | <0.0001 |
| TST (minutes) | 387.5 | 406.5 | 0.0004 | 415.2 | <0.0001 | 417.2 | <0.0001 |
| LPS (minutes)[2] | 34.3 | 30.1 | 0.1836 | 30.8 | 0.2783 | 27.9 | 0.0681 |
| sTST (minutes) | 363.8 | 364.2 | | 379.7 | 0.0470 | 383.0 | 0.0116 |
| sWASO (minutes) | 55.3 | 56.1 | | 50.5 | | 42.1 | 0.0109 |
| LSO (minutes) | 50.9 | 46.9 | | 46.1 | | 44.1 | |
| WTAS (minutes) | 10.2 | 4.1 | 0.1421 | 5.2 | 0.0697 | 2.5 | 0.0105 |

[1]P-value comparing each active treatment versus placebo using Dunnett's test
[2]LPS data were log-transformed prior to analysis Thus, doxepin at 1 mg, 3 mg and 6 mg demonstrated efficacy on sleep maintenance parameters in adult patients with primary sleep maintenance insomnia. This effect appeared to be greater in the doxepin 3 mg and 6 mg dose groups, with both dose groups having comparable sleep maintenance efficacy. Doxepin 1 mg, 3 mg and 6 mg also demonstrated efficacy in delaying early morning awakenings (terminal insomnia) as evidenced by significant reductions in WTAS at the doxepin 6 mg dose level and numerical reductions at the doxepin 1 mg and 3 mg dose levels, all compared to placebo. The doxepin 6 mg dose also demonstrated a numerical improvement on objective sleep onset and a significant improvement on subjective sleep onset. In general, the pattern of the subjective efficacy was consistent with the PSG results.

All doxepin doses were well tolerated and demonstrated an adverse effect profile similar to placebo (See Table 8). There were no significant effects on clinically meaningful alterations observed on next-day residual sedation and sleep architecture.

TABLE 8

Adverse Events by MedDRA System Organ Class
Safety Analysis Set

| System Organ Class/Preferred Term | Placebo (N = 66) Number of Patients | Number of Events | Doxepin HCl 1 mg (N = 66) Number of Patients | Number of Events | Doxepin HCl 3 mg (N = 66) Number of Patients | Number of Events | Doxepin HCl 6 mg (N = 67) Number of Patients | Number of Events |
|---|---|---|---|---|---|---|---|---|
| Patients Reporting at Least One Adverse Event | 6 (9%) | 7 | 9 (14%) | 13 | 5 (8%) | 6 | 8 (12%) | 12 |
| NERVOUS SYSTEM DISORDERS | 3 (5%) | 3 | 4 (6%) | 5 | 2 (3%) | 2 | 4 (6%) | 5 |
| HEADACHE | 3 (5%) | 3 | 3 (5%) | 3 | 0 (0%) | 0 | 1 (1%) | 1 |
| SOMNOLENCE | 0 (0%) | 0 | 1 (2%) | 1 | 1 (2%) | 1 | 3 (4%) | 3 |
| DIZZINESS | 0 (0%) | 0 | 1 (2%) | 1 | 1 (2%) | 1 | 1 (1%) | 1 |
| INFECTIONS AND INFESTATIONS | 2 (3%) | 2 | 1 (2%) | 1 | 1 (2%) | 2 | 0 (0%) | 0 |
| FOLLICULITIS | 0 (0%) | 0 | 0 (0%) | 0 | 1 (2%) | 2 | 0 (0%) | 0 |
| GASTROENTERITIS | 0 (0%) | 0 | 1 (2%) | 1 | 0 (0%) | 0 | 0 (0%) | 0 |
| TOOTH INFECTION | 1 (2%) | 1 | 0 (0%) | 0 | 0 (0%) | 0 | 0 (0%) | 0 |
| URINARY TRACT INFECTION | 1 (2%) | 1 | 0 (0%) | 0 | 0 (0%) | 0 | 0 (0%) | 0 |
| MUSCULOSKELETAL AND CONNECTIVE TISSUE DISORDERS | 0 (0%) | 0 | 2 (3%) | 2 | 1 (2%) | 1 | 0 (0%) | 0 |
| MYALGIA | 0 (0%) | 0 | 1 (2%) | 1 | 1 (2%) | 1 | 0 (0%) | 0 |
| BACK PAIN | 0 (0%) | 0 | 1 (2%) | 1 | 0 (0%) | 0 | 0 (0%) | 0 |
| CARDIAC DISORDERS | 0 (0%) | 0 | 0 (0%) | 0 | 0 (0%) | 0 | 2 (3%) | 2 |
| PALPITATIONS | 0 (0%) | 0 | 0 (0%) | 0 | 0 (0%) | 0 | 1 (1%) | 1 |
| VENTRICULAR EXTRASYSTOLES | 0 (0%) | 0 | 0 (0%) | 0 | 0 (0%) | 0 | 1 (1%) | 1 |
| EYE DISORDERS | 0 (0%) | 0 | 1 (2%) | 1 | 0 (0%) | 0 | 1 (1%) | 1 |
| EYE REDNESS | 0 (0%) | 0 | 0 (0%) | 0 | 0 (0%) | 0 | 1 (1%) | 1 |
| VISION BLURRED | 0 (0%) | 0 | 1 (2%) | 1 | 0 (0%) | 0 | 0 (0%) | 0 |
| PSYCHIATRIC DISORDERS | 0 (0%) | 0 | 0 (0%) | 0 | 0 (0%) | 0 | 2 (3%) | 2 |
| ABNORMAL DREAMS | 0 (0%) | 0 | 0 (0%) | 0 | 0 (0%) | 0 | 1 (1%) | 1 |
| ANXIETY | 0 (0%) | 0 | 0 (0%) | 0 | 0 (0%) | 0 | 1 (1%) | 1 |
| RESPIRATORY, THORACIC AND MEDIASTINAL DISORDERS | 0 (0%) | 0 | 1 (2%) | 1 | 0 (0%) | 0 | 1 (1%) | 1 |
| NASAL CONGESTION | 0 (0%) | 0 | 1 (2%) | 1 | 0 (0%) | 0 | 0 (0%) | 0 |
| PHARYNGOLARYNGEAL PAIN | 0 (0%) | 0 | 0 (0%) | 0 | 0 (0%) | 0 | 1 (1%) | 1 |
| SKIN AND SUBCUTANEOUS TISSUE DISORDERS | 0 (0%) | 0 | 1 (2%) | 1 | 1 (2%) | 1 | 0 (0%) | 0 |
| DERMATITIS | 0 (0%) | 0 | 1 (2%) | 1 | 1 (2%) | 1 | 0 (0%) | 0 |
| GASTROINTESTINAL DISORDERS | 0 (0%) | 0 | 1 (2%) | 1 | 0 (0%) | 0 | 0 (0%) | 0 |
| STOMACH DISCOMFORT | 0 (0%) | 0 | 1 (2%) | 1 | 0 (0%) | 0 | 0 (0%) | 0 |
| GENERAL DISORDERS AND ADMINISTRATION SITE CONDITIONS | 0 (0%) | 0 | 1 (2%) | 1 | 0 (0%) | 0 | 0 (0%) | 0 |
| GAIT ABNORMAL | 0 (0%) | 0 | 1 (2%) | 1 | 0 (0%) | 0 | 0 (0%) | 0 |
| IMMUNE SYSTEM DISORDERS | 0 (0%) | 0 | 0 (0%) | 0 | 0 (0%) | 0 | 1 (1%) | 1 |
| HYPERSENSITIVITY | 0 (0%) | 0 | 0 (0%) | 0 | 0 (0%) | 0 | 1 (1%) | 1 |
| INVESTIGATIONS | 1 (2%) | 2 | 0 (0%) | 0 | 0 (0%) | 0 | 0 (0%) | 0 |
| BLOOD PRESSURE INCREASED | 1 (2%) | 1 | 0 (0%) | 0 | 0 (0%) | 0 | 0 (0%) | 0 |
| CARDIAC MURMUR | 1 (2%) | 1 | 0 (0%) | 0 | 0 (0%) | 0 | 0 (0%) | 0 |

[1] At each level of summation (overall, system organ class, preferred term), patients reporting more than one adverse event per treatment are counted only once. Each event is assigned to the most recent treatment received prior to onset.

Comparison of Results in Elderly vs. Non-Elderly (Ages 18-64) Patients

The primary efficacy result, WTDS, was surprisingly significantly decreased in elderly patients who were given 1 milligram of doxepin. In contrast, there was no significant effect of 1 mg doxepin in non-elderly adults. Doxepin at 3 milligrams and 6 milligrams exhibited significant reductions in WTDS in both patient populations.

In addition to the primary efficacy results, two secondary efficacy results were also affected at lower doxepin dosages in elderly versus non-elderly patients: LPS and WTAS. LPS exhibited significant decreases in elderly patients at both 3 milligrams and 6 milligrams doxepin, while no effect of doxepin on LPS was observed in non-elderly patients at these dosages. In addition, WTAS exhibited significant decreases in elderly patients at both 3 milligrams and 6 milligrams doxepin, while a significant decrease in WTAS in non-elderly patients was only observed with 6 milligrams doxepin.

There were statistically significant improvements in mean CGI (Clinician-rated) severity of illness and therapeutic effect scores at Night 85 in both doxepin treatment groups compared with placebo. There were statistically significant improvements in CGI (Subject-rated) therapeutic effect scores compared with placebo in each doxepin group at each visit for one or more parameters. No such effects were observed in the non-elderly adults at any dose.

We claim:

1. A method for treating insomnia characterized by difficulties with sleep maintenance, the method comprising:
    identifying a first adult patient 18 to 64 years of age in need of treatment of insomnia;
    identifying a second adult patient 65 years of age or older in need of treatment of insomnia who is susceptible to one or more side effects caused by a sleep medication, the side effects comprising one or more of nervous system side effects, psychiatric side effects, respiratory side effects, skin side effects, musculoskeletal side effects, connective tissue side effects or central nervous system side effects;
    recognizing that a daily dosage of 6 mg doxepin or a pharmaceutically acceptable salt thereof provides a statistically significant decrease in wake time during sleep (WTDS) in a group of adult patients 18 to 64 years of age but does not provide a statistically significant effect on next-day residual sedation in a group of adult patients 18 to 64 years of age;

administering to the first adult patient a daily dosage of 6 mg doxepin or a pharmaceutically acceptable salt thereof;

recognizing that a daily dosage of 3 mg doxepin or a pharmaceutically acceptable salt thereof provides statistically significant decrease in wake time during sleep (WTDS) and in wake after sleep onset (WASO) in a group of elderly patients 65 years of age or older and does not provide a statistically significant effect on next-day residual sedation in a group of elderly patients 65 years of age or older;

administering to the second adult patient an initial daily dosage of 3 mg doxepin or a pharmaceutically acceptable salt thereof;

evaluating whether a desired improvement in sleep is achieved by the second adult patient at the initial daily dosage; and increasing the daily dosage of the second adult patient to 6 mg only if the desired improvement in sleep is not achieved, wherein the initial daily dosage of 3 mg is administered to the second adult patient for at least 15 consecutive days.

2. The method of claim 1, wherein the initial daily dosage of 3 mg is administered to the second adult patient for up to 85 days.

3. A method for treating insomnia, the method comprising:

identifying a first adult patient 18 to 64 years of age in need of treatment of insomnia;

identifying a second adult patient 65 years of age or older in need of treatment of insomnia who is susceptible to one or more side effects caused by a sleep medication, the side effects comprising one or more of nervous system side effects, psychiatric side effects, respiratory side effects, skin side effects, musculoskeletal side effects, connective tissue side effects or central nervous system side effects;

administering to the first adult patient a daily dosage of 6 mg doxepin or a pharmaceutically acceptable salt thereof; and administering to the second adult patient a daily dosage of 3 mg doxepin or a pharmaceutically acceptable salt thereof, wherein the daily dosage of 3 mg provides a statistically significant reduction in latency to persistent sleep (LPS) in a group of elderly patients 65 years of age or older, and wherein the daily dosage of 3 mg is administered to the second adult patient for at least 15 consecutive days.

4. The method of claim 3, wherein the daily dosage of 3 mg is administered to the second adult patient for at least 15 days.

5. The method of claim 3, wherein the daily dosage of 3 mg is administered to the second adult patient for up to 85 days.

6. The method of claim 3, further comprising evaluating whether a desired improvement in sleep is achieved by the second adult patient at the daily dosage of 3 mg and increasing the daily dosage of the second adult patient to 6 mg if the desired improvement in sleep is not achieved.

7. The method of claim 3, wherein administration of a daily dosage of 3 mg doxepin or a pharmaceutically acceptable salt thereof to a group of adult patients 18 to 64 years of age does not provide a statistically significant reduction in latency to persistent sleep.

8. The method of claim 3, wherein the insomnia comprises insomnia characterized by difficulties with sleep maintenance.

9. The method of claim 3, wherein the daily dosage of 3 mg does not provide a statistically significant effect on next-day residual sedation in a group of elderly patients 65 years of age or older.

10. The method of claim 3, wherein the daily dosage of 6 mg does not provide a statistically significant effect on next-day residual sedation in a group of adult patients 18 to 64 years of age.

11. The method of claim 1, further comprising recognizing that a daily dosage of 3 mg doxepin or a pharmaceutically acceptable salt thereof provides a statistically significant reduction in latency to persistent sleep (LPS) in a group of elderly patients 65 years of age or older.

12. The method of claim 1, wherein the central nervous side effects comprises at least one of a somnolence, headache, dizziness, lethargy or balance disorder.

13. The method of claim 1, wherein the psychiatric side effect comprises at least one of anxiety, confusion and abnormal dreams.

14. The method of claim 1, wherein the psychiatric side effect comprises anxiety or abnormal dreams.

15. The method of claim 3, wherein the central nervous side effect comprises at least one of a somnolence, headache, dizziness, lethargy or balance disorder.

16. The method of claim 3, wherein the psychiatric side effect comprises at least one of anxiety, confusion and abnormal dreams.

17. The method of claim 3, wherein the psychiatric side effect comprises anxiety or abnormal dreams.

18. A method for treating chronic insomnia, the method comprising:

identifying a first adult patient 18 to 64 years of age in need of treatment of insomnia;

identifying a second adult patient 65 years of age or older in need of treatment of insomnia who is susceptible to one or more side effects caused by a sleep medication, the side effects comprising one or more of nervous system side effects, psychiatric side effects, respiratory side effects, skin side effects, musculoskeletal side effects, connective tissue side effects or central nervous system side effects;

administering to the first adult patient a daily dosage of 6 mg doxepin or a pharmaceutically acceptable salt thereof; and administering to the second adult patient a daily dosage of 3 mg doxepin or a pharmaceutically acceptable salt thereof for up to 85 days, wherein the daily dosage of 3 mg provides a statistically significant reduction in latency to persistent sleep (LPS) in a group of elderly patients 65 years of age or older, and wherein the daily dosage of 3 mg is administered to the second adult patient for at least 15 consecutive days.

* * * * *